(12) United States Patent
Cannara et al.

(10) Patent No.: US 11,426,759 B2
(45) Date of Patent: Aug. 30, 2022

(54) APPARATUS AND METHOD FOR BATCH SPRAY COATING OF SURGICAL NEEDLES

(71) Applicant: Ethicon, Inc., Somerville, NJ (US)

(72) Inventors: Alexander M. Cannara, Roseland, NJ (US); Frank Richard Cichocki, Jr., Easton, PA (US); Duan Li Ou, Warren, NJ (US)

(73) Assignee: Ethicon, Inc., Raritan, NJ (US)

( * ) Notice: Subject to any disclaimer, the term of this patent is extended or adjusted under 35 U.S.C. 154(b) by 59 days.

(21) Appl. No.: 16/781,586

(22) Filed: Feb. 4, 2020

(65) Prior Publication Data
US 2020/0171532 A1 Jun. 4, 2020

Related U.S. Application Data

(62) Division of application No. 15/621,007, filed on Jun. 13, 2017, now Pat. No. 10,589,313.

(51) Int. Cl.
| *B05D 1/02* | (2006.01) |
|---|---|
| *A61B 17/06* | (2006.01) |
| *B21G 1/00* | (2006.01) |
| *B05B 13/02* | (2006.01) |
| *A61B 17/00* | (2006.01) |

(52) U.S. Cl.
CPC .......... *B05D 1/02* (2013.01); *A61B 17/06066* (2013.01); *B05B 13/025* (2013.01); *B21G 1/006* (2013.01); *A61B 2017/00526* (2013.01); *A61B 2017/0608* (2013.01)

(58) Field of Classification Search
CPC .... A61B 17/06; A61B 17/06066; A23G 1/26; A61L 31/10; B05D 1/02; B65B 35/00
See application file for complete search history.

(56) References Cited

U.S. PATENT DOCUMENTS

| 3,695,223 | A | 10/1972 | Dunham et al. |
|---|---|---|---|
| 5,536,527 | A | 7/1996 | Prasad |
| 5,628,826 | A | 5/1997 | Prasad |
| 5,661,954 | A * | 9/1997 | Ivanov ................... B65B 35/26 |
| | | | 53/118 |
| 7,939,615 | B2 | 5/2011 | Ou |
| 8,883,245 | B2 | 11/2014 | Cichocki et al. |
| 9,434,857 | B2 | 9/2016 | Ou |
| 2006/0292271 | A1 | 12/2006 | King |
| 2014/0277120 | A1 | 9/2014 | Cichocki |
| 2015/0367039 | A1 | 12/2015 | Ou |
| 2016/0143325 | A1 | 5/2016 | Heinzen et al. |

FOREIGN PATENT DOCUMENTS

| EP | 0667124 A | 8/1995 |
|---|---|---|
| EP | 0908144 A | 7/2004 |
| EP | 1531009 A | 5/2005 |
| WO | 2011/056451 A | 5/2011 |

OTHER PUBLICATIONS

International search report and written opinion dated Sep. 13, 2018, for international application PCT/IB2018/053398.

* cited by examiner

*Primary Examiner* — Dah-Wei D. Yuan
*Assistant Examiner* — Andrew J Bowman
(74) *Attorney, Agent, or Firm* — Amir Bishara

(57) ABSTRACT

Novel apparatus and methods for coating surgical needles in batch processes are disclosed. The apparatus and methods are particularly useful for applying uniform silicone lubricious coatings to surgical needles in bulk quantities using a novel separation and spray coating system and method.

22 Claims, 21 Drawing Sheets

APPARATUS AND METHOD FOR BATCH SPRAY COATING OF SURGICAL NEEDLES

This application is a division of copending U.S. patent application Ser. No. 15/621,007, which was filed on Jun. 13, 2017. The complete disclosures of the aforementioned related U.S. patent applications are hereby incorporated herein by reference.

FIELD OF THE INVENTION

The field of art to which this invention pertains is surgical needles, more particularly apparatus and methods for coating surgical needles with lubricious coatings in batch processes.

BACKGROUND OF THE INVENTION

Surgical sutures having attached surgical needles are well known in the art and provide a fundamental and essential means for various wound closure applications, including for example, approximating and closing incisions and lacerations. It is desirable to coat surgical needles with lubricious coatings to facilitate the passage of the needle through various types of tissues for multiple passes. Ease of penetration of the surgical needles through tissue is a critical, required property and is known to facilitate a wound closure procedure by providing the surgeon or medical professional with consistent performance during the suturing or wound closure process in which the needle readily passes through tissue with a minimal amount of force applied. Such surgical needles in combination with the skills of the surgeon are known to produce superior patient outcomes. Surgical needles are conventionally coated with a variety of known silicone-based coating solutions. The coating solutions may be applied in a variety of ways including dipping, spraying, brushing, etc. The needles may be singulated by mounting on strips prior to coating or may be batch coated. Batch coating processes typically are dipping processes wherein a batch of needles is placed in a wire basket, and then the basket and needles are subsequently immersed in a bath containing a liquid silicone coating composition. The basket containing the wet needles is subsequently removed from the coating bath and excess silicone is drained from the needles to the extent possible. Then the batch of wet needles is transferred to a suitable shallow container such as a tray for further additional conventional processing including curing and interim packaging. Although batch coating processes provide an adequate means to apply silicone coatings to a large number of surgical needles, there are several deficiencies associated with the use of these coating processes. First of all, the needles must be handled and moved after the batch coating application when the coatings are still wet to subsequent steps in the coating process including, for example, curing. It is known that handling needles having wet silicone coatings can result in damage to the integrity of the coatings resulting in coating defects such as globbiness and/or discontinuity in the coating. These defects can adversely affect the penetration performance of the surgical needles. Additionally, in a batch dipping process it is known that the wet silicone coatings can withdraw from the piercing tips of the needles due to the surface energy and low viscosity, which provides ample mobility to the silicone coating solution. The decreased amount of silicone coating on the piercing tips is a major factor associated with adverse needle penetration performance. Another disadvantage of the existing bulk dip-coating silicone coating processes is that they are known to be inefficient due to excess usage of expensive silicone coating solutions. A significant disadvantage of such existing processes relates to the associated economic inefficiencies in the manufacturing process resulting from significant numbers of needles having deficient or defective coatings which must be identified and discarded.

Accordingly, there is a need in this art for novel silicone coating processes that can be used with batch needle manufacturing processes and which provide superior needle coatings and associated improved needle performance, as well as manufacturing and cost efficiencies.

SUMMARY OF THE INVENTION

Therefore, a novel apparatus and method for spray coating bulk surgical needles in batch processes are disclosed.

The novel apparatus for spray coating bulk surgical needles has a needle separation tower for receiving bulk surgical needles and separating the needles. The needle tower has frame having a top, a bottom, a first end and a second end. A top tower belt, an intermediate tower belt, and a bottom tower belt are mounted to the frame, each belt having a first end and a second end, and a top and a bottom. A bulk needle receiving structure is associated with the top, first end of the frame for receiving a plurality of bulk surgical needles and directing the needles to the top tower belt. An angled baffle member is mounted to the tower frame for directing needles from the top tower belt to the intermediate tower belt. There is an overspill barrier member for directing needles from the intermediate tower belt to the bottom tower belt. A first belt stepper motor engages the top tower belt, a second belt stepper motor engages the intermediate tower belt, and a third belt stepper motor engaging the bottom tower belt. A rotating member is mounted to the top of the tower frame at the second end over the top tower belt for engaging needles on the top tower belt. There is an upper paper conveyor for receiving needles from the bottom tower belt of the needle separation tower. The upper paper conveyor has a first end and a second end, an upper frame, an upper absorbent belt, an upper drive roll, an upper take-up roll, an upper first end roll and a second magnetic end roll for engaging needles. A stepper motor engages the upper drive roll. There is a lower paper conveyor for receiving needles from the upper paper conveyor. The lower paper conveyor has a first end and second end, a lower frame, a lower absorbent belt, a lower drive roll, a lower take-up roll, a lower first end roll and a lower second end roll for engaging needles. There is a stepper motor engaging the lower drive roll. At least one spray nozzle is moveably mounted over the upper and lower paper conveyors for spraying a silicone lubricious coating onto surgical needles on the upper and lower absorbent belt.

Another aspect is a novel method of using the novel bulk spraying apparatus to coat a plurality of needles with a lubricious silicone coating in a bulk process These and other aspects and advantages of the present invention will become more apparent from the following description and accompanying drawings.

DETAILED DESCRIPTION OF THE INVENTION

Figure 1A:
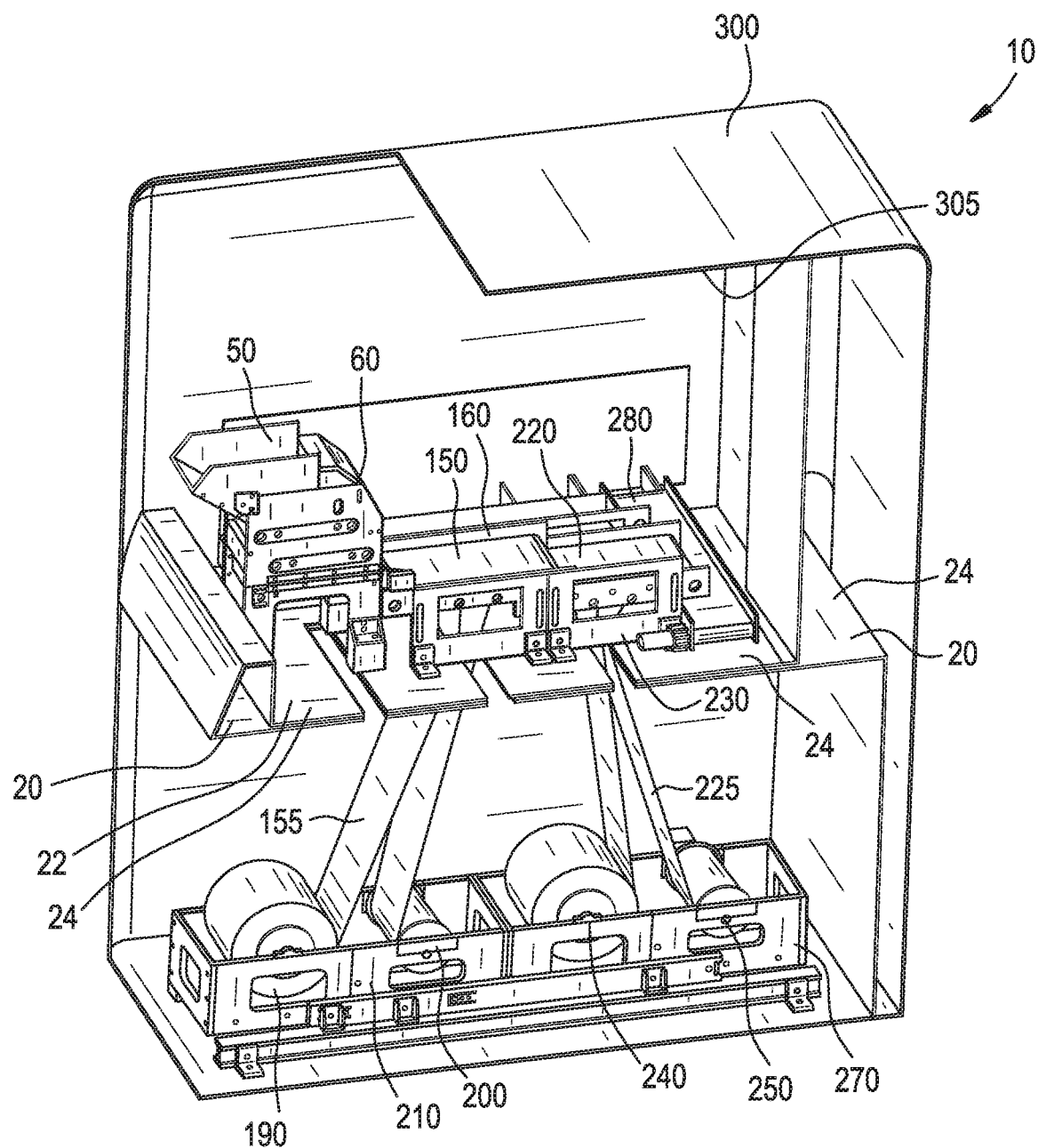
FIG. 1A is a perspective view of a bulk needle spray coating apparatus of the present invention; the enclosure or outer cell is shown partially cut away, and the silicone spray heads are not shown.
Figure 1B:
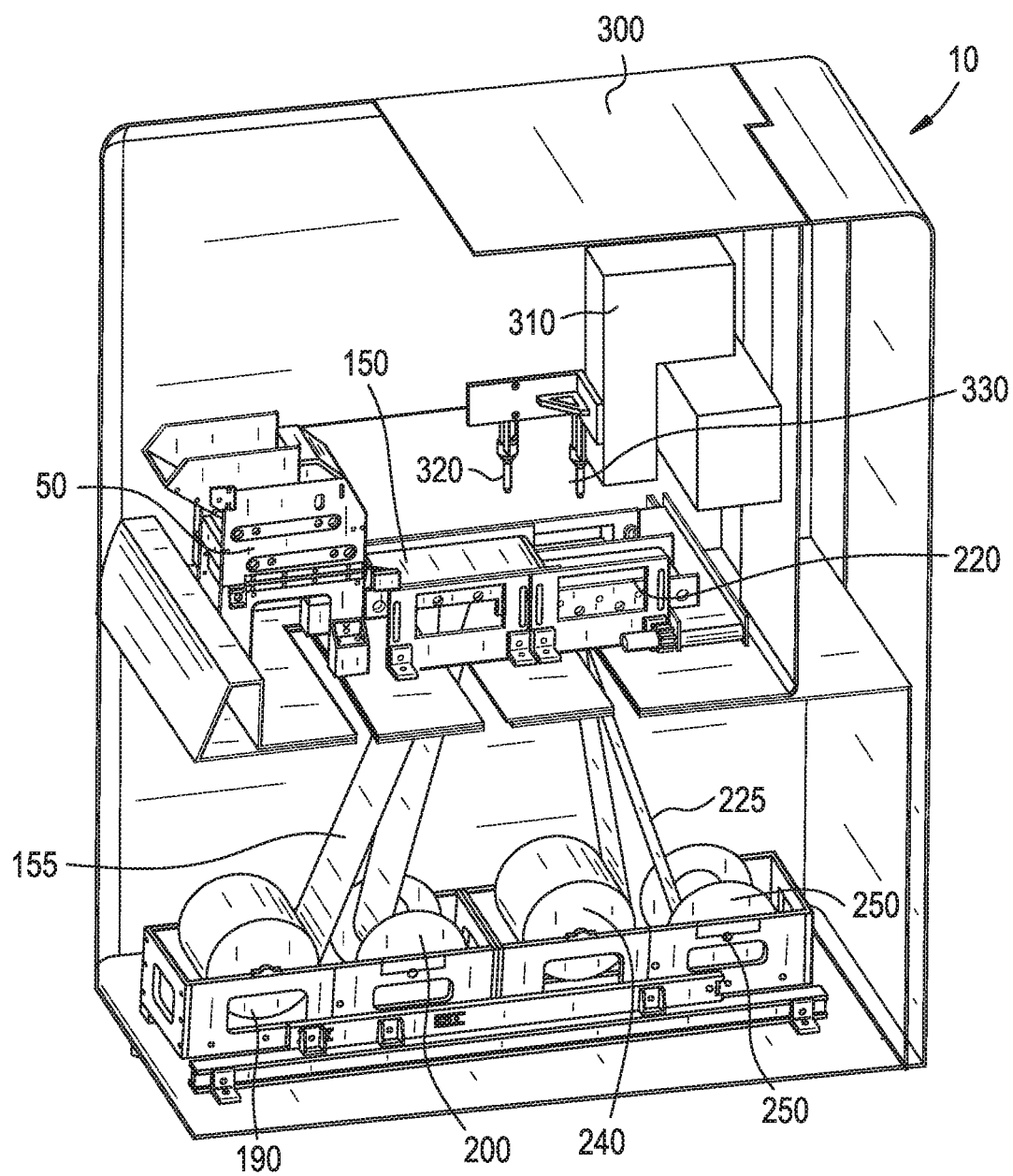
FIG. 1B illustrates the apparatus of FIG. 1A with the spray heads shown.
Figure 1C:
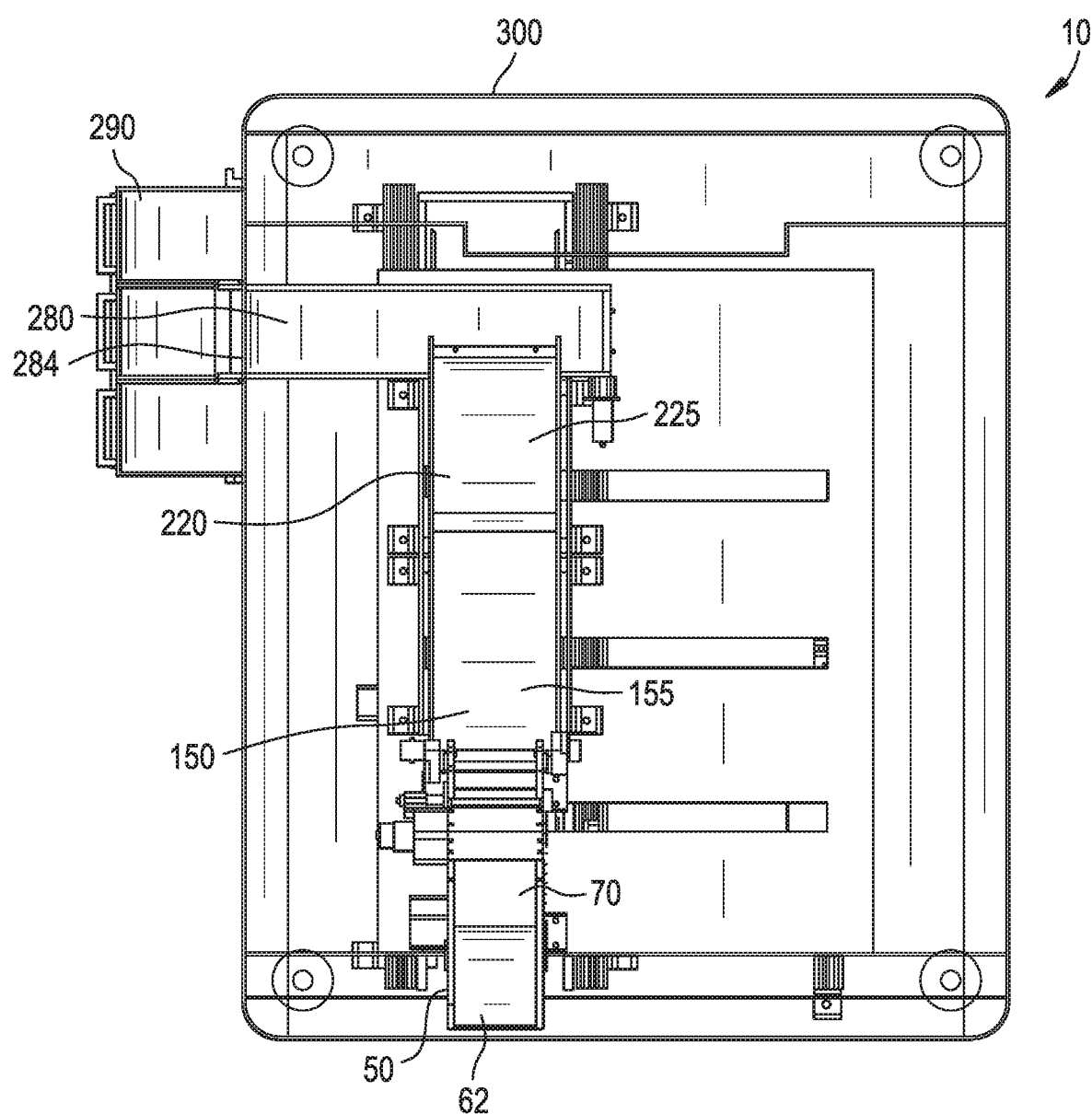
FIG. 1C is a top view of the apparatus of FIG. 1A.
Figure 1D:
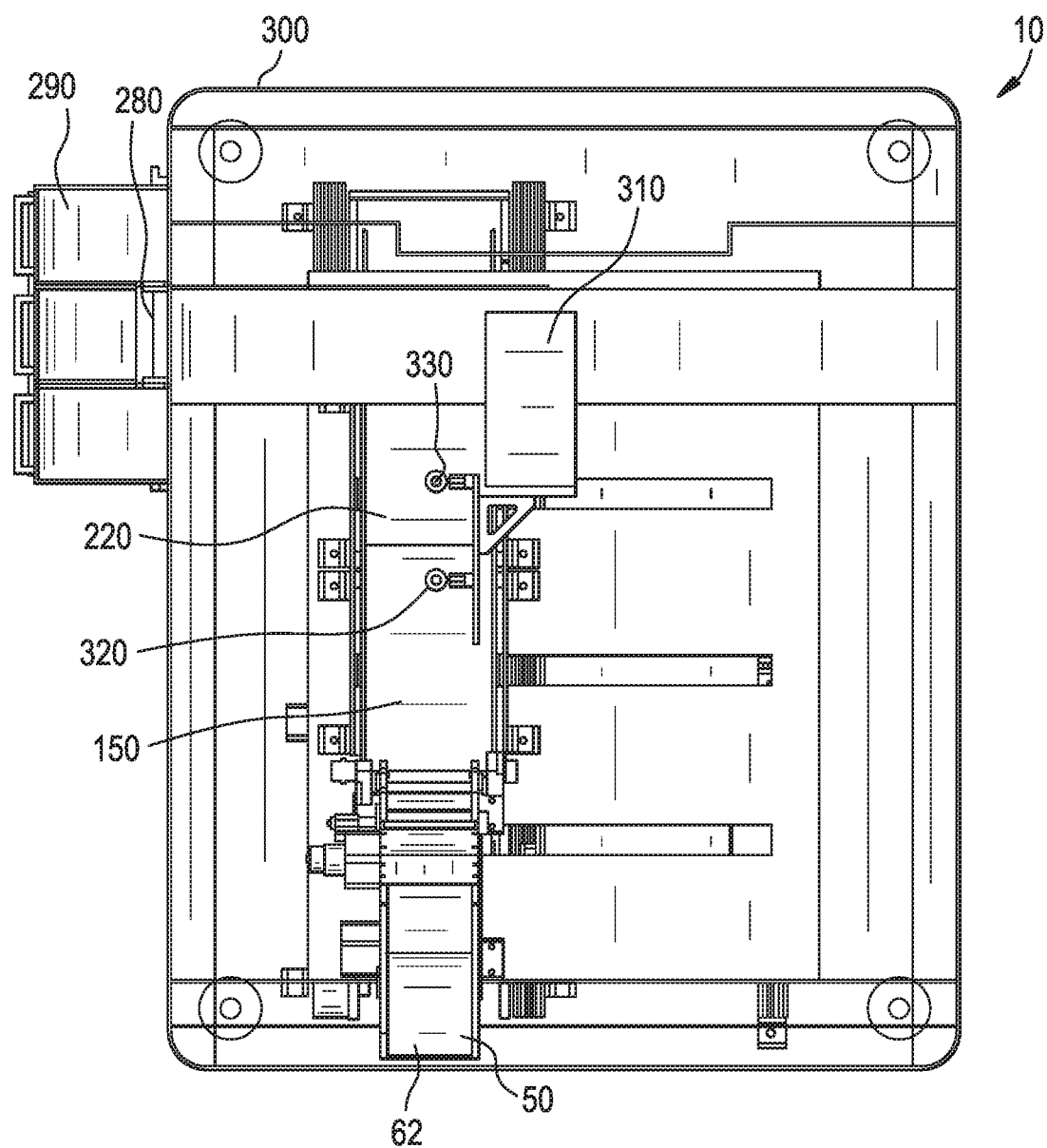
FIG. 1D is a top view of the apparatus of FIG. 1B.

The novel bulk needle spray coating apparatus and process of the present invention is used to apply lubricious silicone-based coatings to the surfaces of loose or bulk surgical suture needles. Coated surgical needles produced using this novel apparatus and process are provided with many advantages including the improved ability to penetrate tissue with minimal resistance, and reduced defects in the coatings. In addition, the apparatus and process of the present invention provide production efficiencies and cost savings by reducing the amounts of silicone coating solution required to coat bulk needles, and by decreasing or substantially eliminating needles having defective coatings, which would need to be discarded as waste.

In contrast to the bulk dipping and immersion processes of the prior art, the novel bulk spray process of the present invention utilizes a spray system that provides a fine mist of silicone coating solution in combination with absorbable paper belts and a magnetic engagement roller to provide uniform, defect-free coatings. This fine mist of silicone has the advantage of producing a surface coating that is not overly wet as it lands on the needles. Due to the fine droplet size of the coating solution mist, most of the solvents in the silicone coating solution are dispersed while the mist is airborne which allows the individual droplets to thicken and create a "fog" of silicone. This produces and results in what is believed to be a nearly dry applied coating on the surface of the needles that is more tolerant of handling and resistant to damage in its uncured state than the current conventional batch processes. Such conventional processes produce a wetter more liquid-like applied coating that is more easily susceptible to damage during handling. The fine mist is also advantageous in that because of the thickening of the coating in mid-air due to the reduction of solvent content, the piercing points of the surgical needles can be provided with an optimal coating which is critical to needle penetration performance. Needle tip coating deficiencies are a significant drawback of the bulk dipping process of the prior art. During a typical batch coat process of the prior art where the needles are dipped into a tank of liquid silicone, the wet coating will draw back away from the points of the needles due to the surface tension and lower viscosity of the fluid which has a higher solvent content than the sprayed mist when it interacts with the needle surface. Although conventional spray coating processes for bulk surgical needles are known in this art, there are disadvantages associated with their use including obtaining a uniform coating on all surfaces of the needles, maintaining adequate throughput, achieving the proper coating mist or fog to coat the needles yet prevent excessive overspray buildup, and minimizing waste. Another advantage to the novel bulk spray process of the present invention is the elimination of the step of "Water Plugging" of the needles prior to the coating process. With the conventional processes, prior to the immersion of the needles into the silicone bath, the needles are placed into a vacuum chamber and the air removed. Then, water is introduced as the vacuum is released. This allows the bore of the needle barrel to be filled with a quantity of water to prevent silicone from obscuring the hole. Once the needles are dip-coated and cured, the water evaporates out of the hole, leaving it free of silicone and ready to accept the suture. With the novel bulk spray process of the present invention, this water-plugging step is not necessary, as the blind hole in the needle does not allow the pressurized spray of silicone to enter. This eliminates a step from the preparation of the needles, and thereby increases the throughput and process efficiency of the novel bulk spray process.

The silicone coating compositions that can be used with the apparatus and process of the present invention will include, but are not limited to, hydroxy-terminated polydimethylsiloxane cross-linked with polymethylhydrosiloxane. Examples of this class of materials include commercially available silicone products such as Nusil MED 4162 and Dow Corning MDX 4159. Another useful coating is vinyl-terminated polydimethylsiloxane cross-linked with polymethylhydrosiloxane catalyzed by platinum catalyst as described in U.S. Pat. No. 9,434,857. Those skilled in the art will appreciate that other conventional silicone coatings, although not preferred, may be utilized as well in the practice of the present invention.

Figure 2:
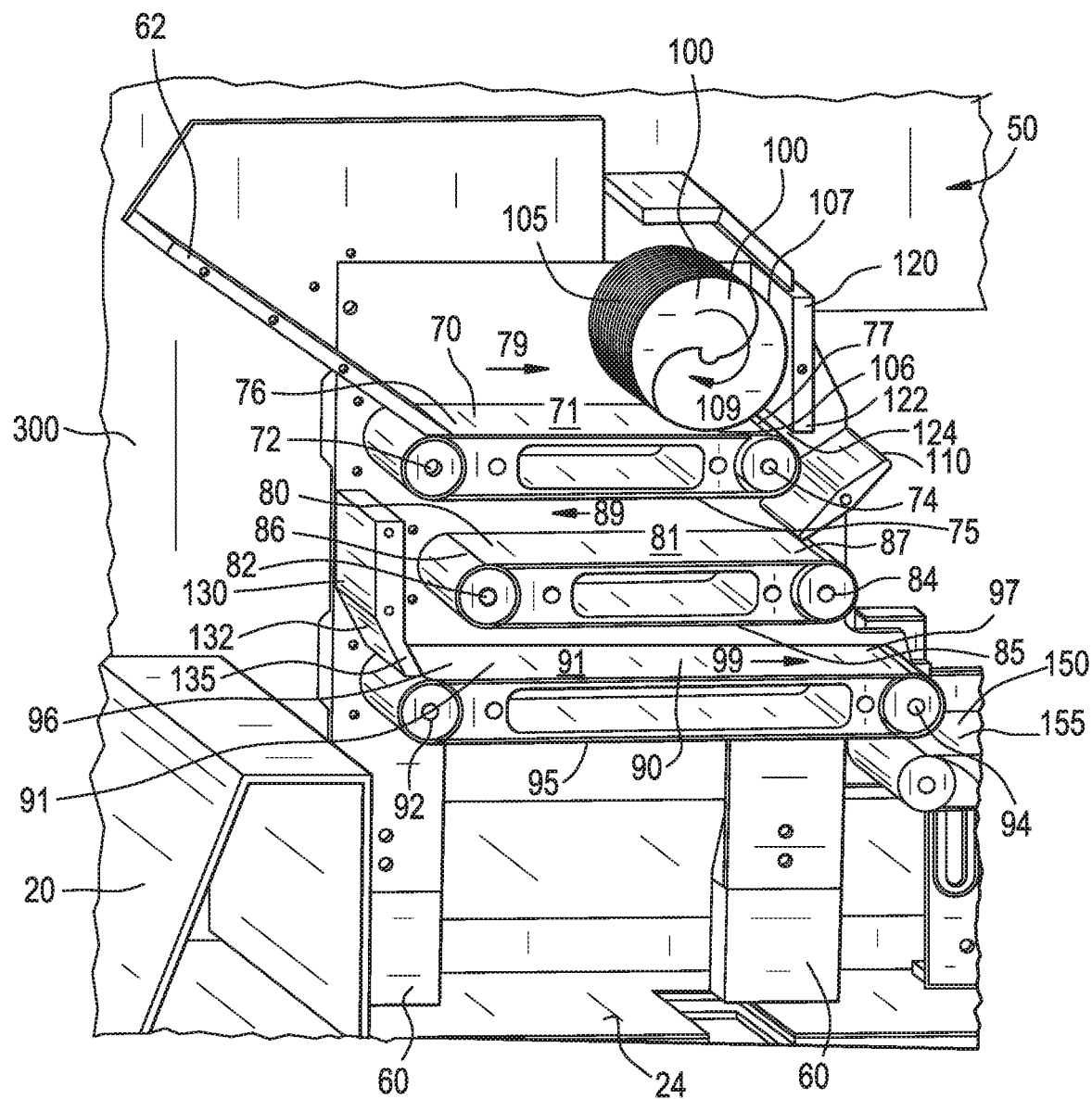
FIG. 2 is a perspective, cut-away side view of the needle separation tower of the apparatus of FIG. 1
Figure 3:
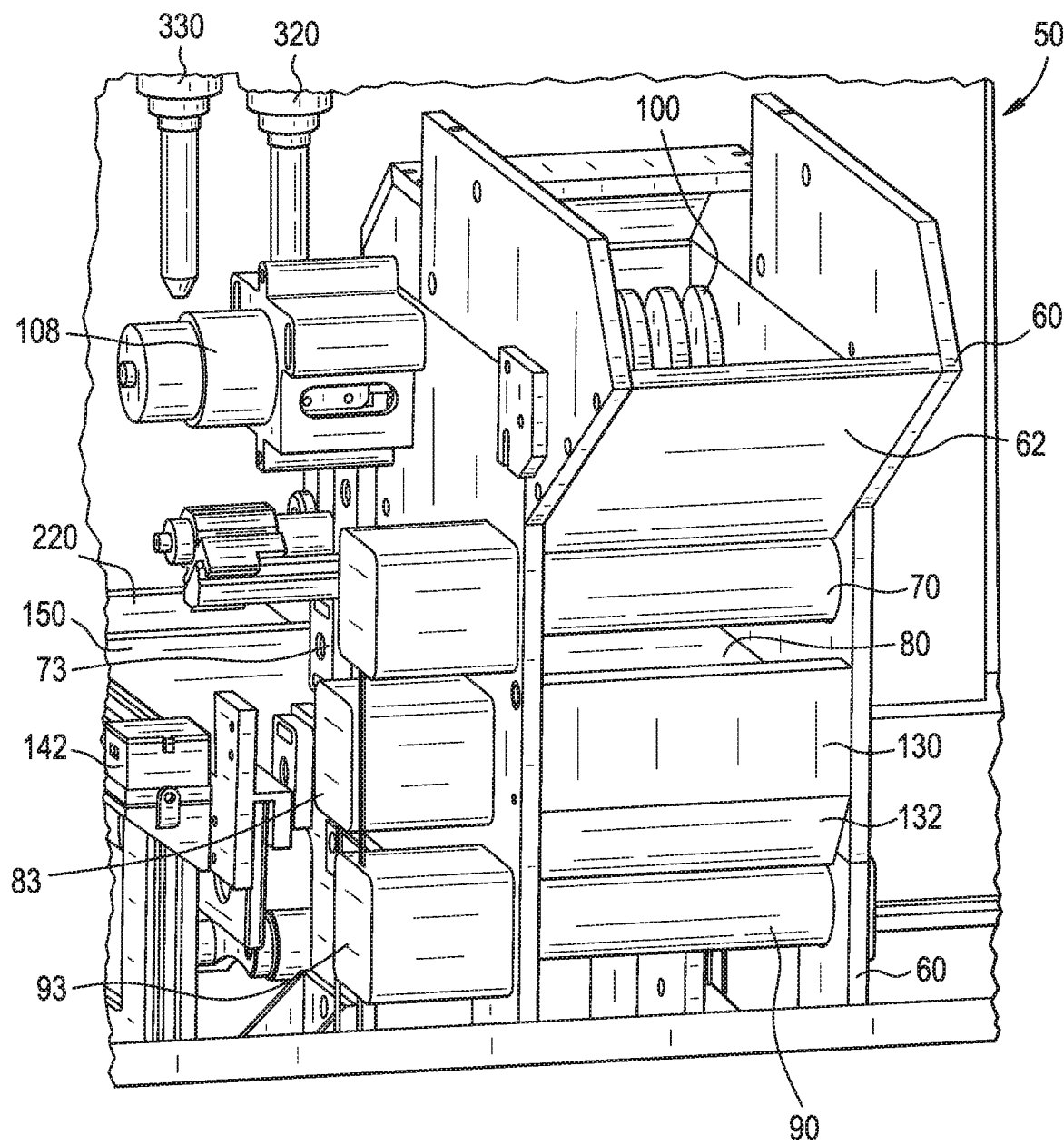
FIG. 3 is an end view of the needle separation tower of FIG. 2.
Figure 4A:
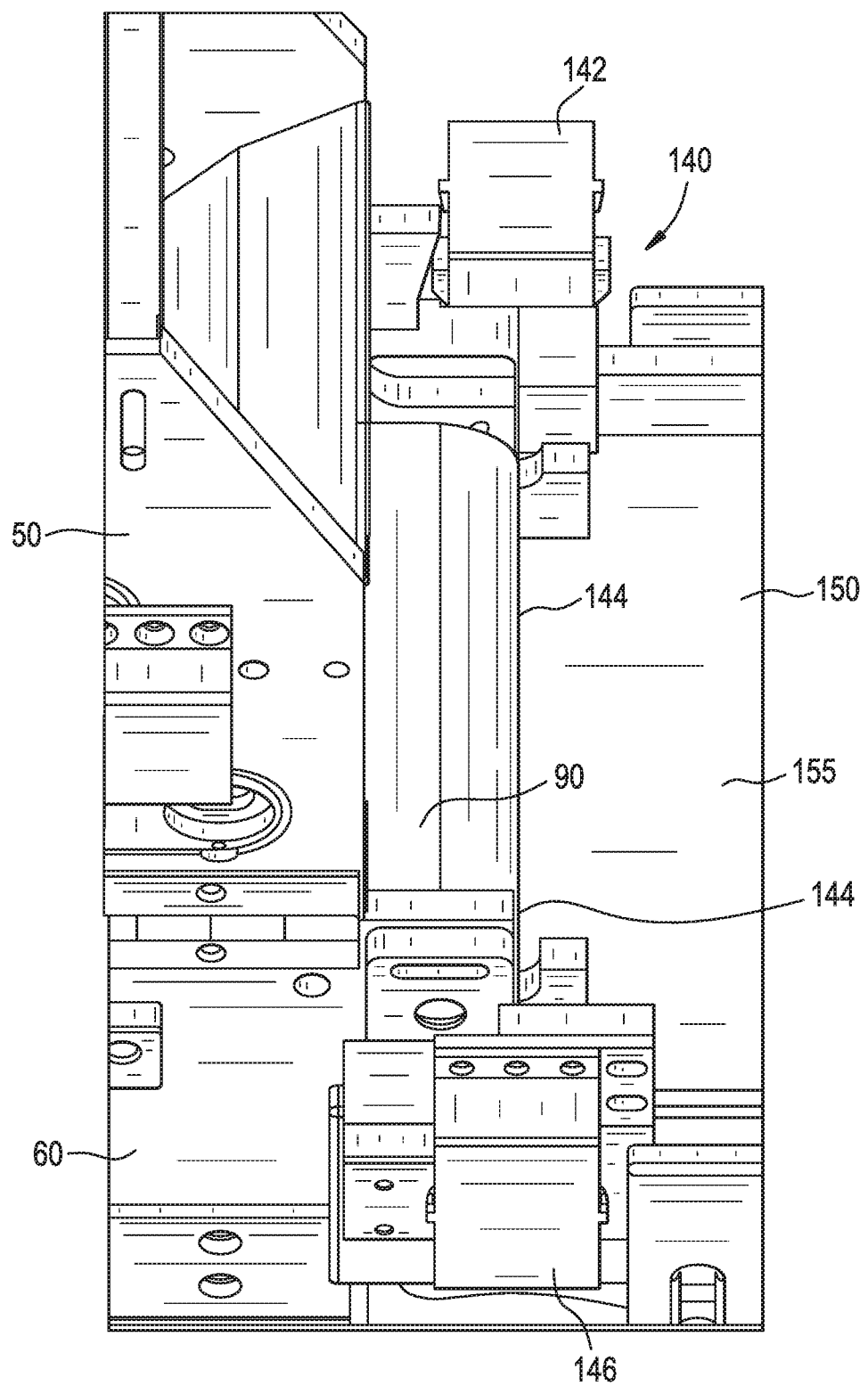
FIG. 4A is a partial top view of the apparatus of FIG. 1 showing the end of the bottom needle tower belt from the needle separation tower located over the first end of the upper paper conveyor and the upper paper belt.
Figure 4B:
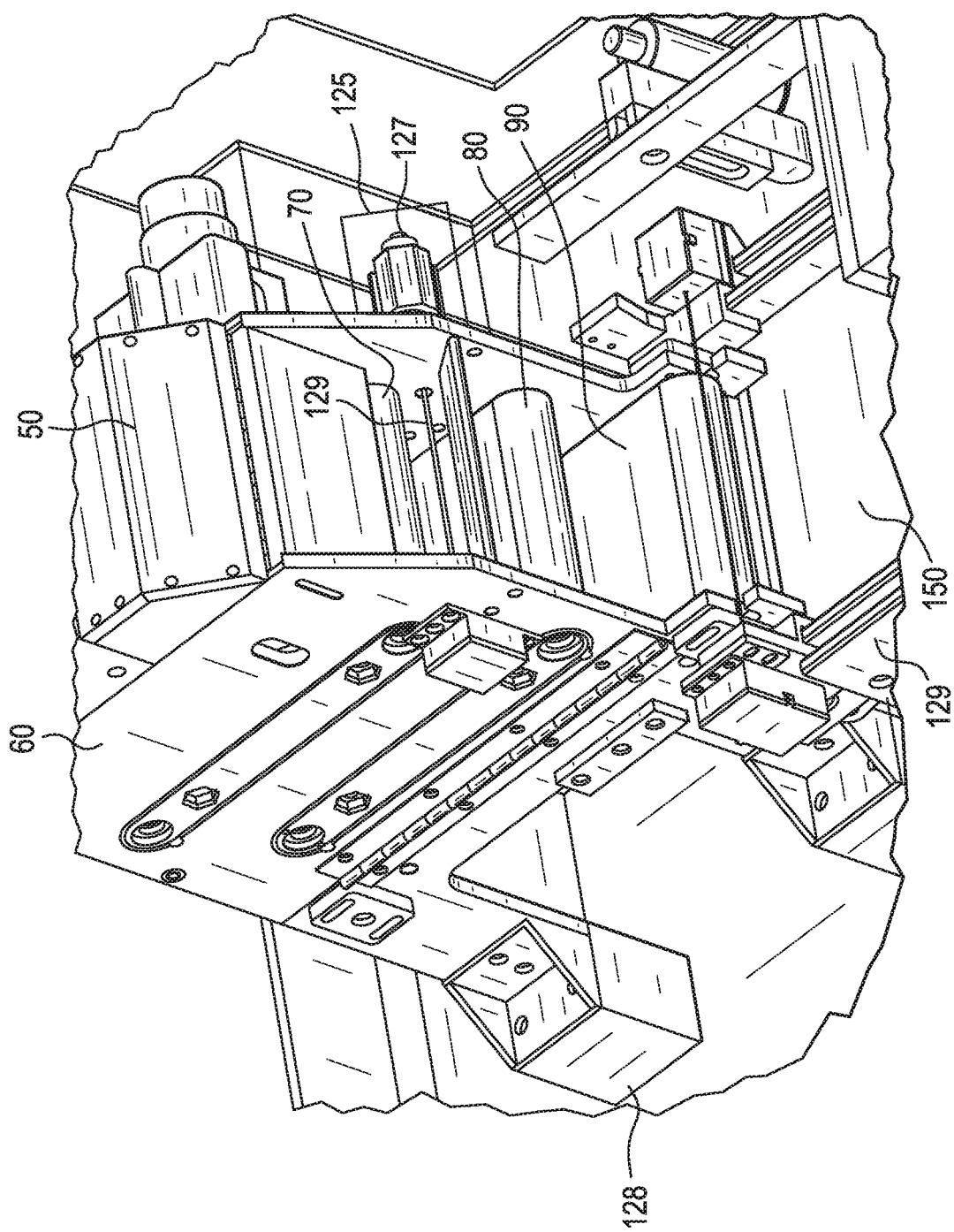
FIG. 4B is a partial perspective end view of the needles separator tower of FIG. 2, showing the needle discharge end of the separator tower.
Figure 5:
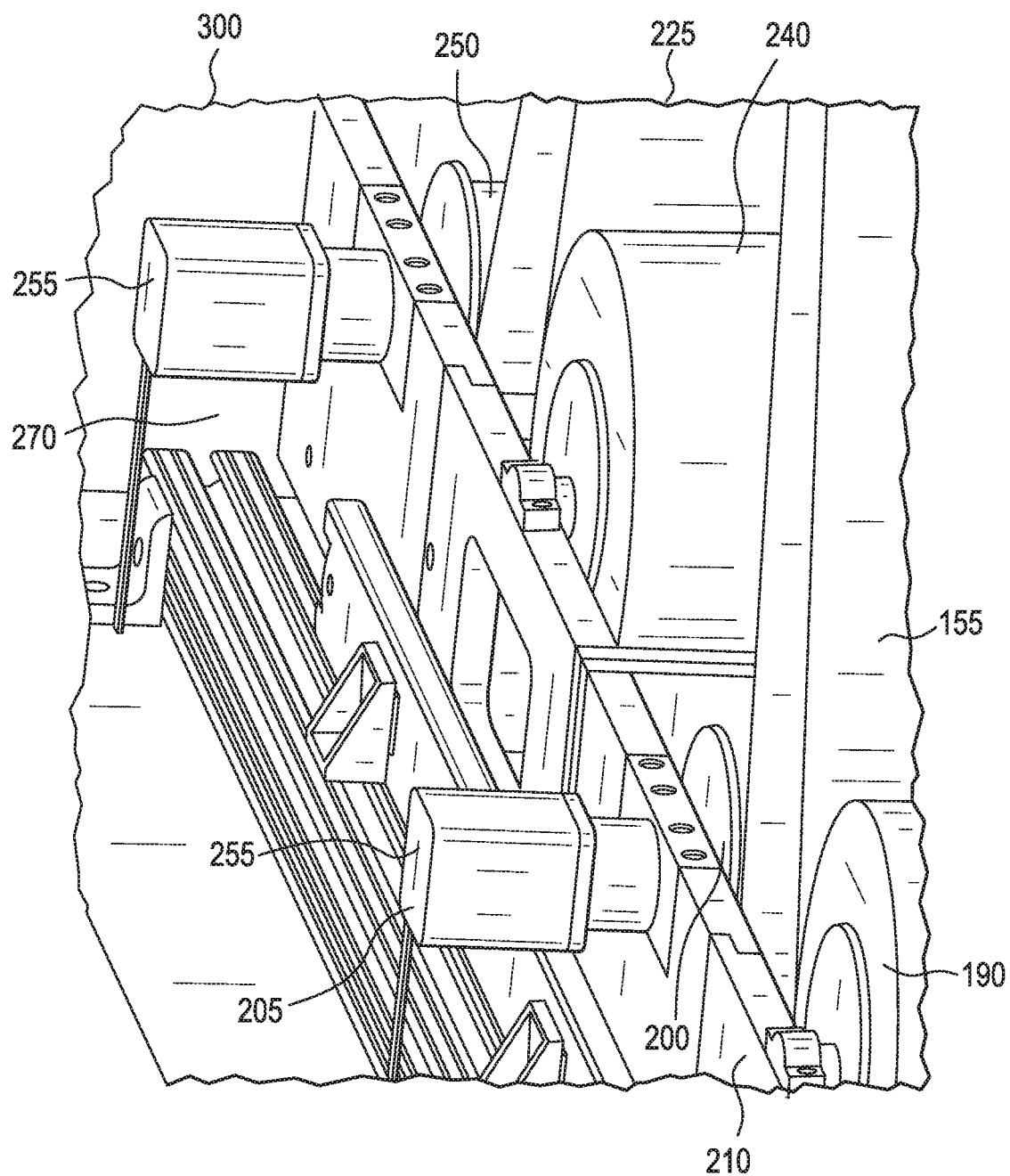
FIG. 5 is a partial perspective view of the bottoms of the upper and lower paper conveyors showing the drive motors that engage the driven paper rolls.
Figure 6:
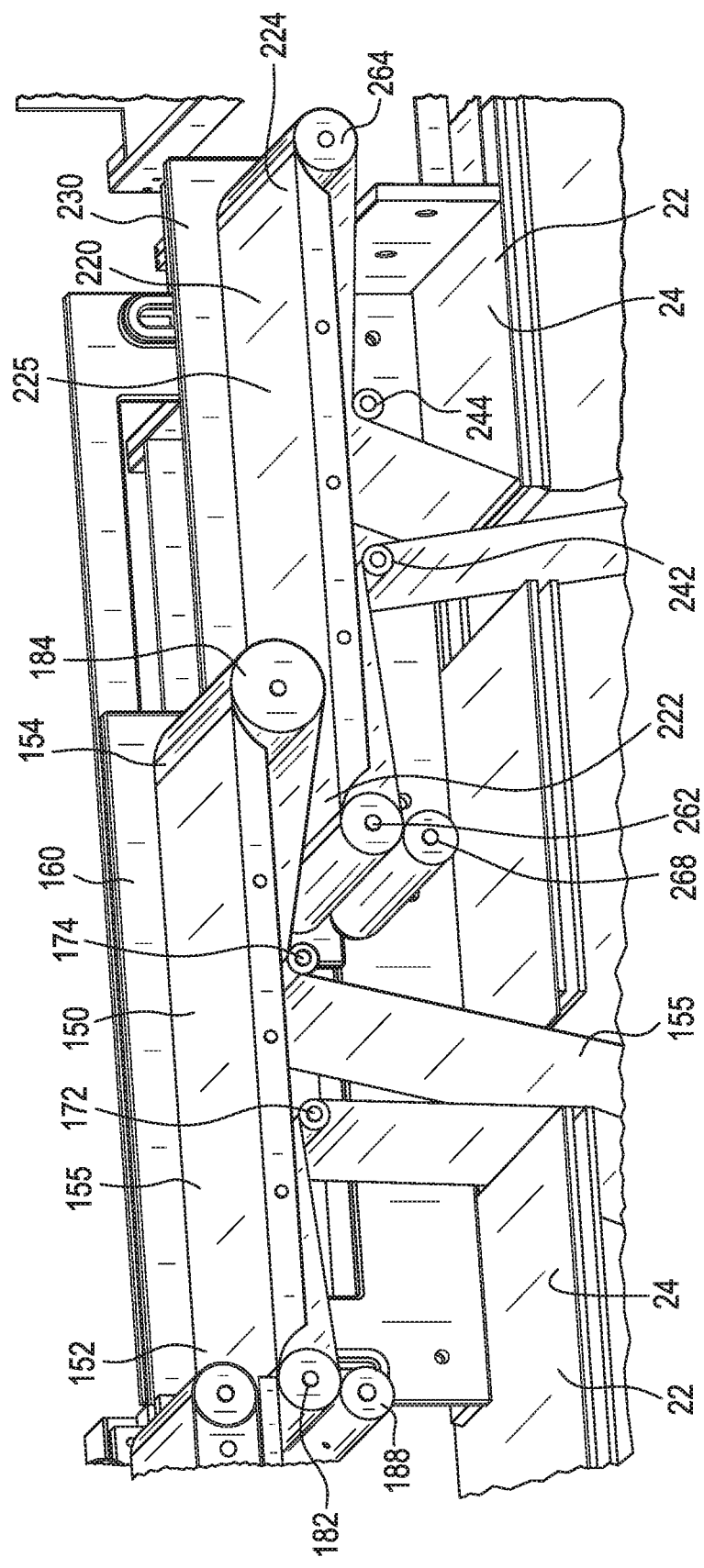
FIG. 6 is a partial perspective view showing the roller arrangement for the upper and lower paper belts.
Figure 7:
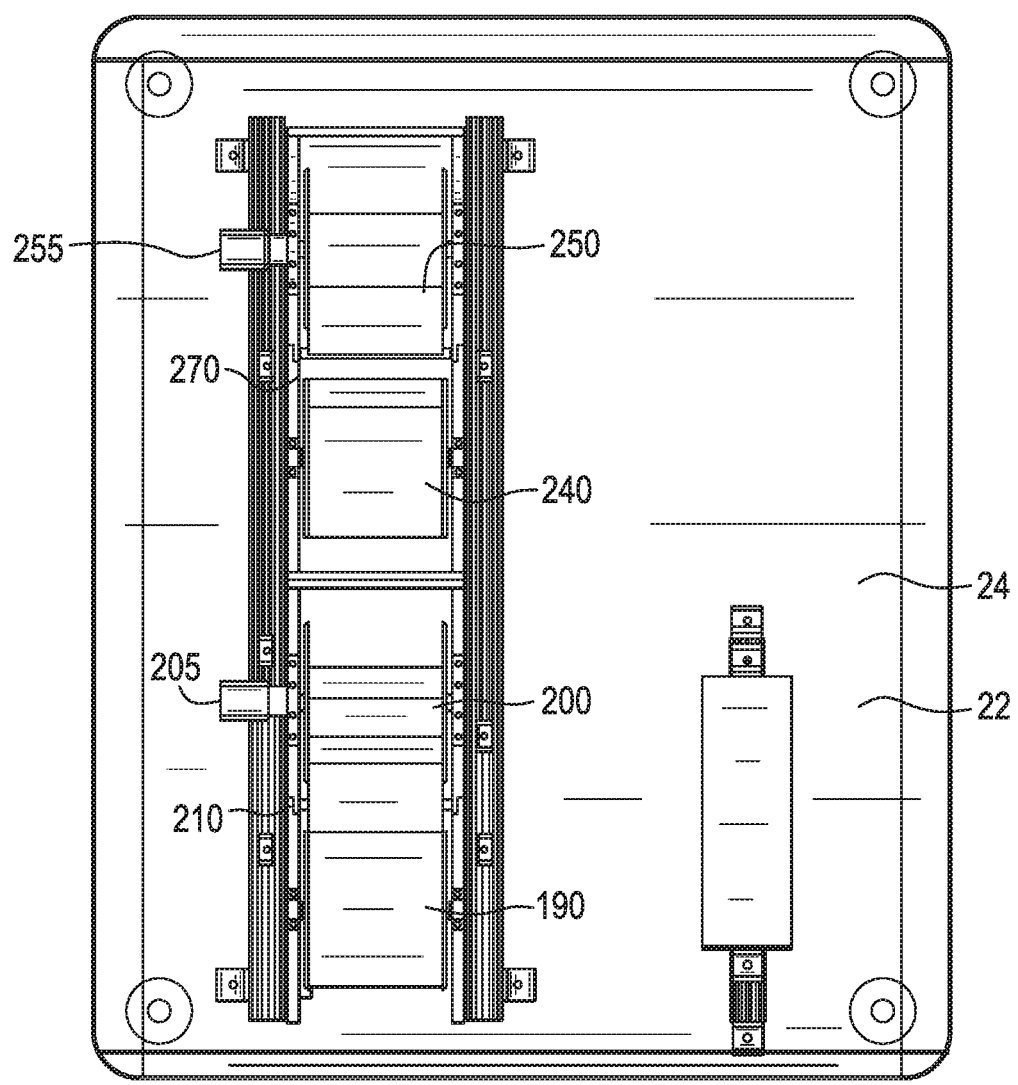
FIG. 7 is a top view of the lower frames of the upper and lower paper conveyors showing the drive spools and the driven spools.
Figure 8:
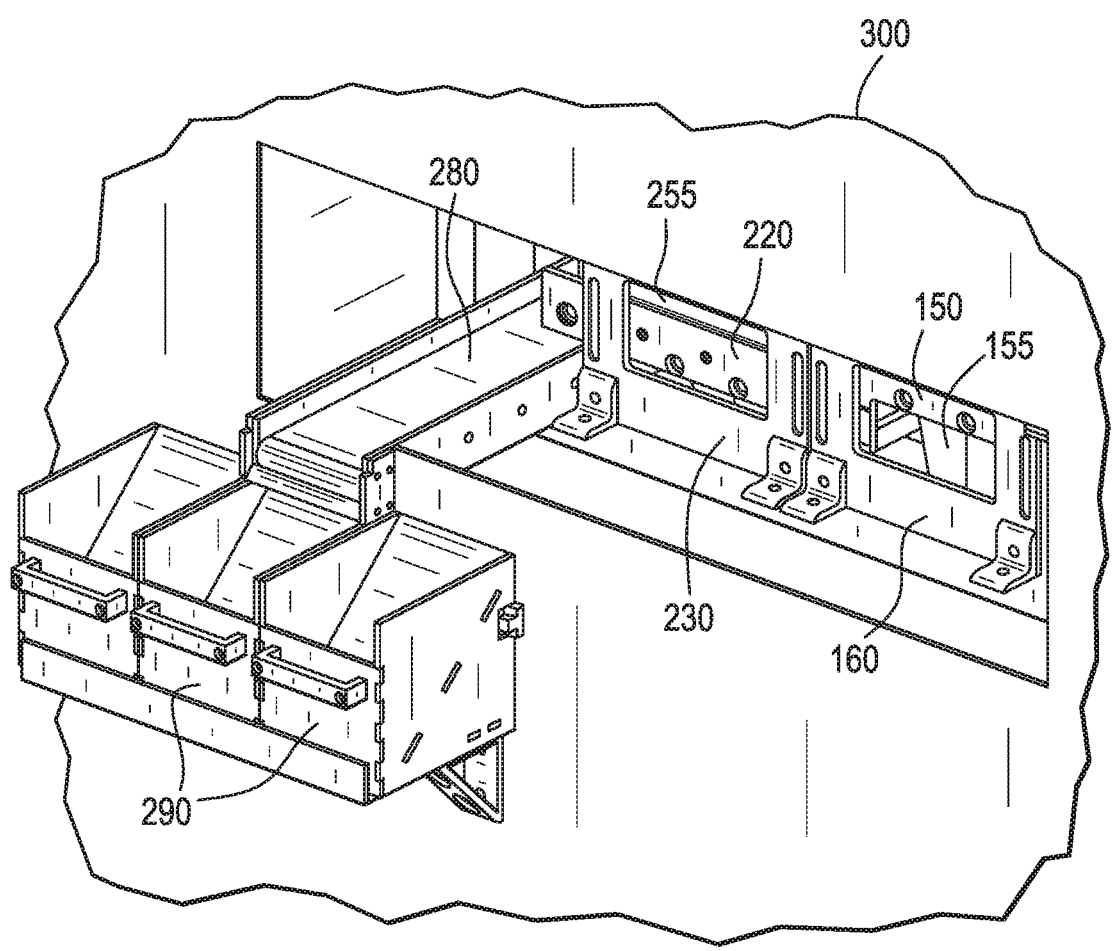
FIG. 8 is a perspective view showing the discharge end of the discharge conveyor belt over needle collection containers.
Figure 9:
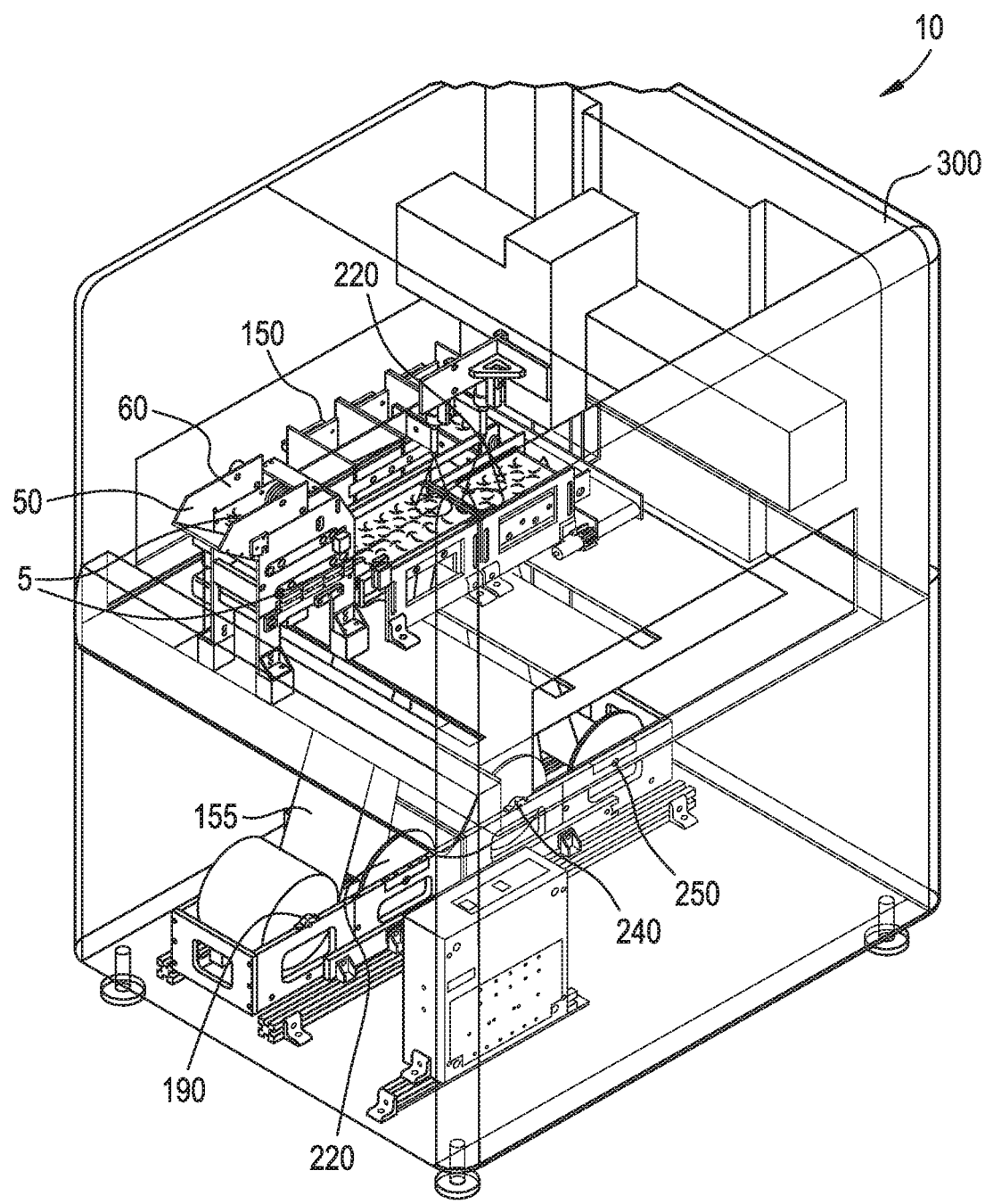
FIG. 9 is a perspective view of the bulk needle spray coating apparatus of the present invention processing bulk surgical needles to apply silicone coatings showing the flow of needles through the separation and coating processes.
Figure 10:
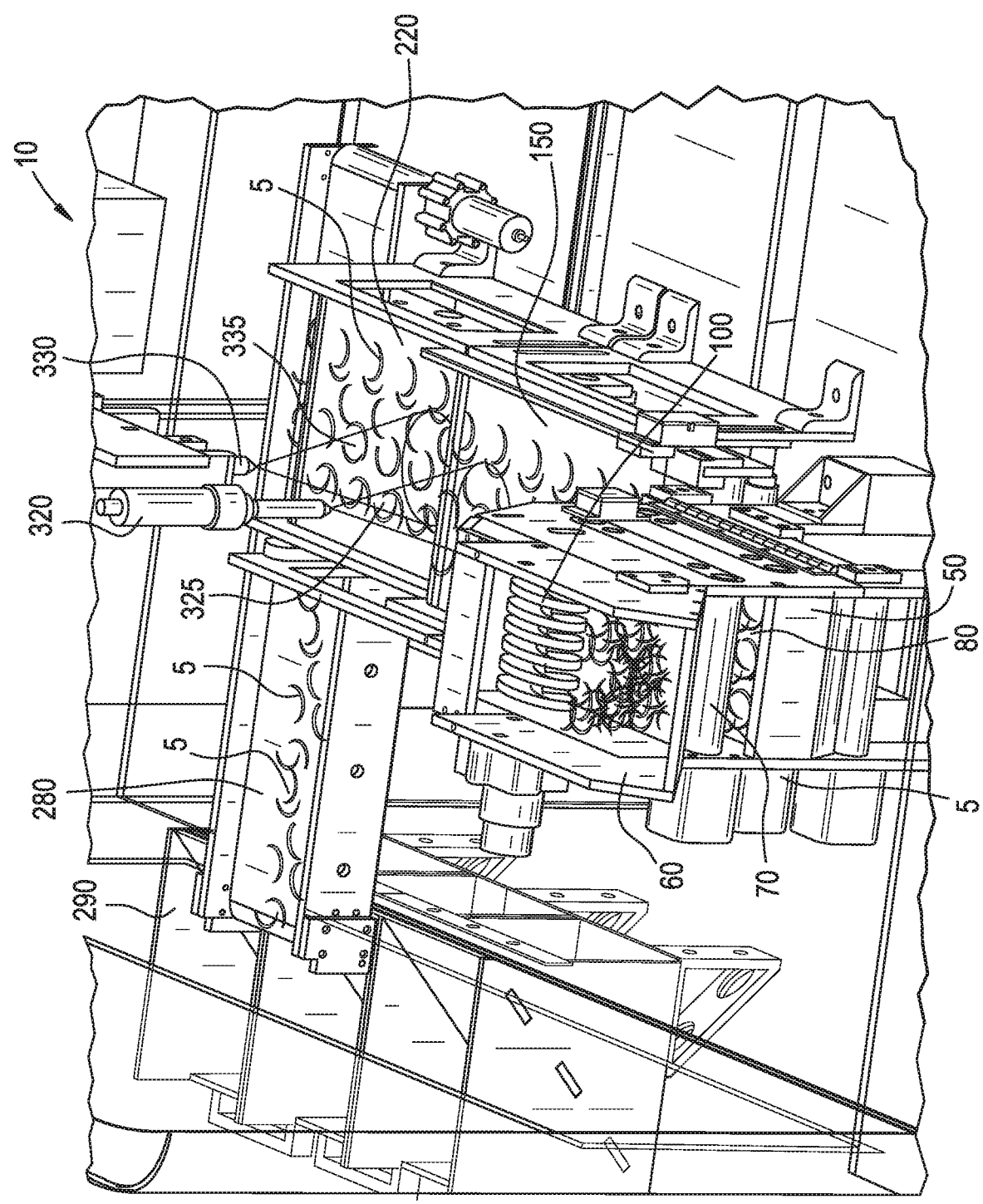
FIG. 10 is a top perspective view of the apparatus of FIG. 9 showing needles in the needle separation tower and on the upper and lower paper conveyors and the discharge conveyor; the spray nozzles are seen emitting a spray cone of silicone coating solution.
Figure 11:
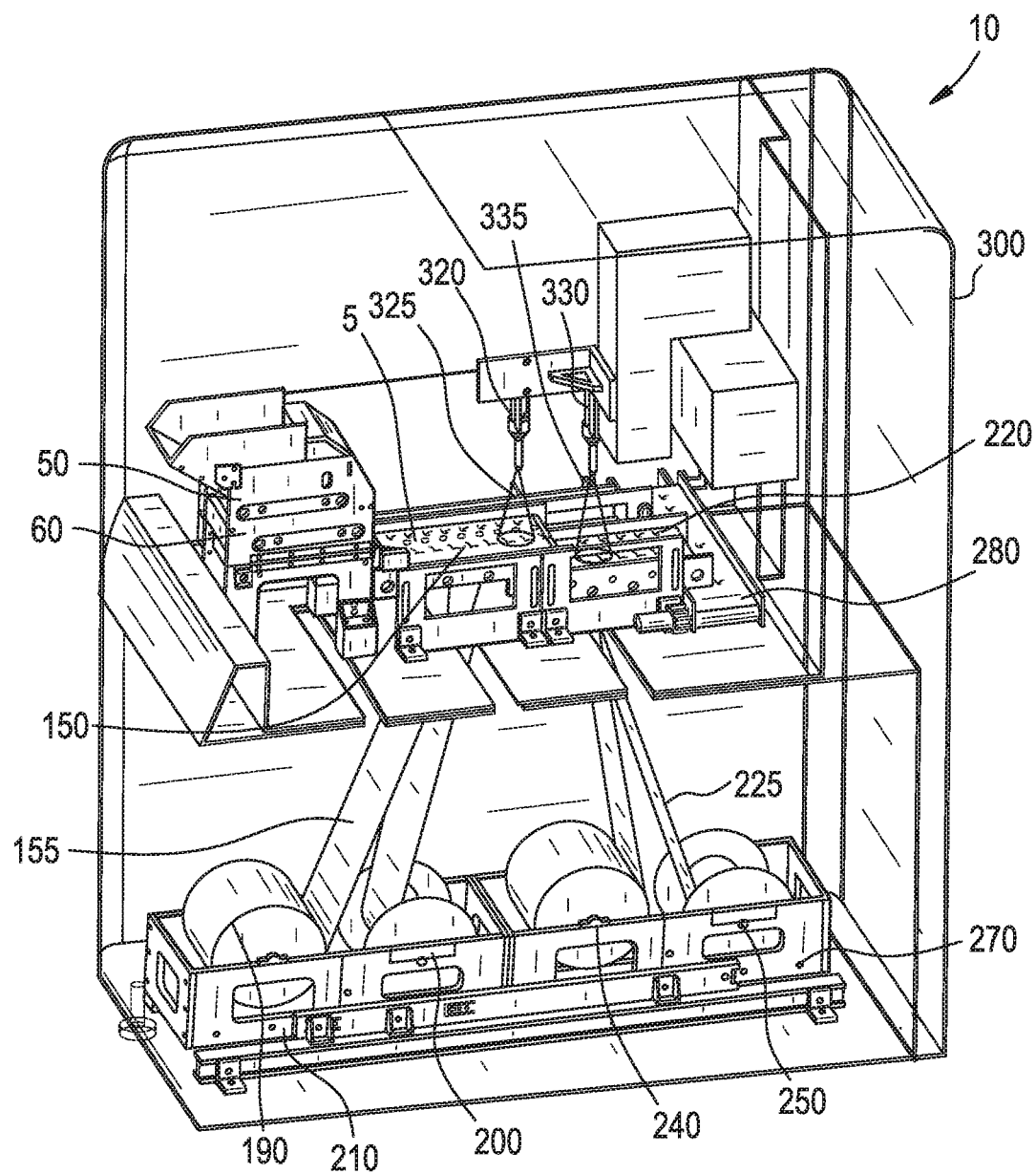
FIG. 11 is a side perspective view of the apparatus of FIG. 9, showing needles being processed and spray coated.
Figure 12:
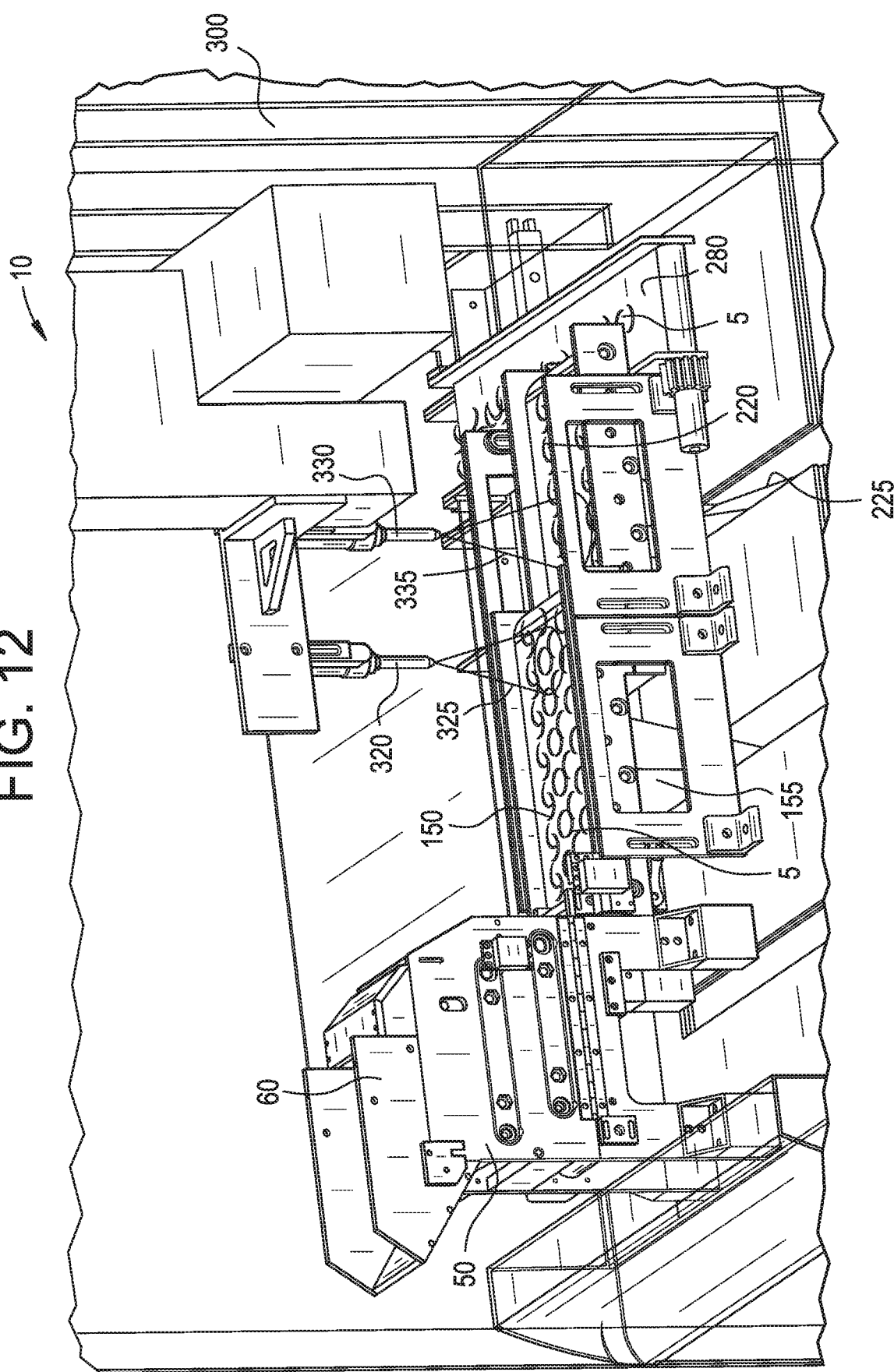
FIG. 12 is a magnified partial view of the apparatus of FIG. 11.
Figure 13:
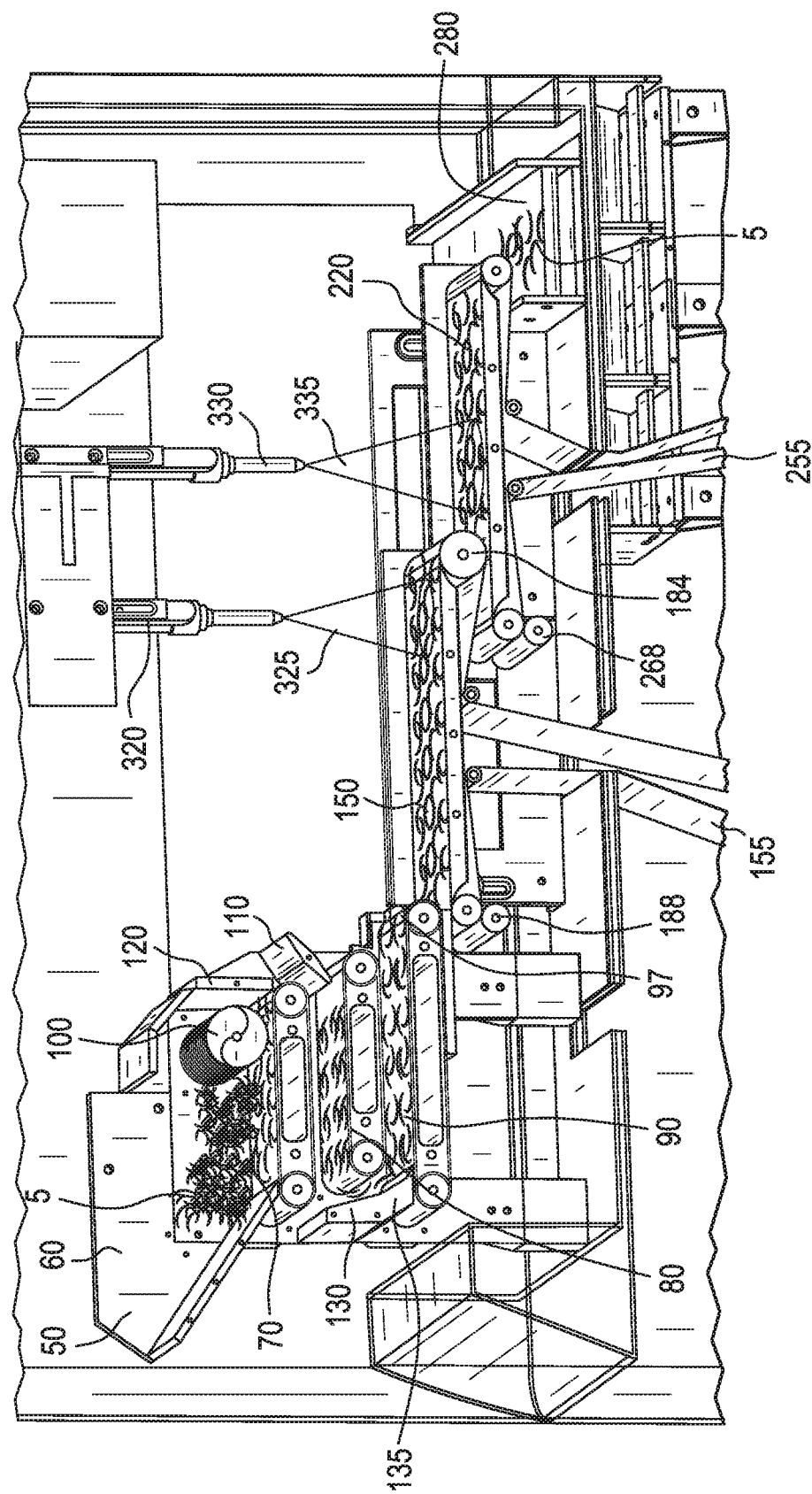
FIG. 13 is a perspective view of the apparatus of FIG. 11 showing a cut-away view of the needle separation tower.
Figure 14:
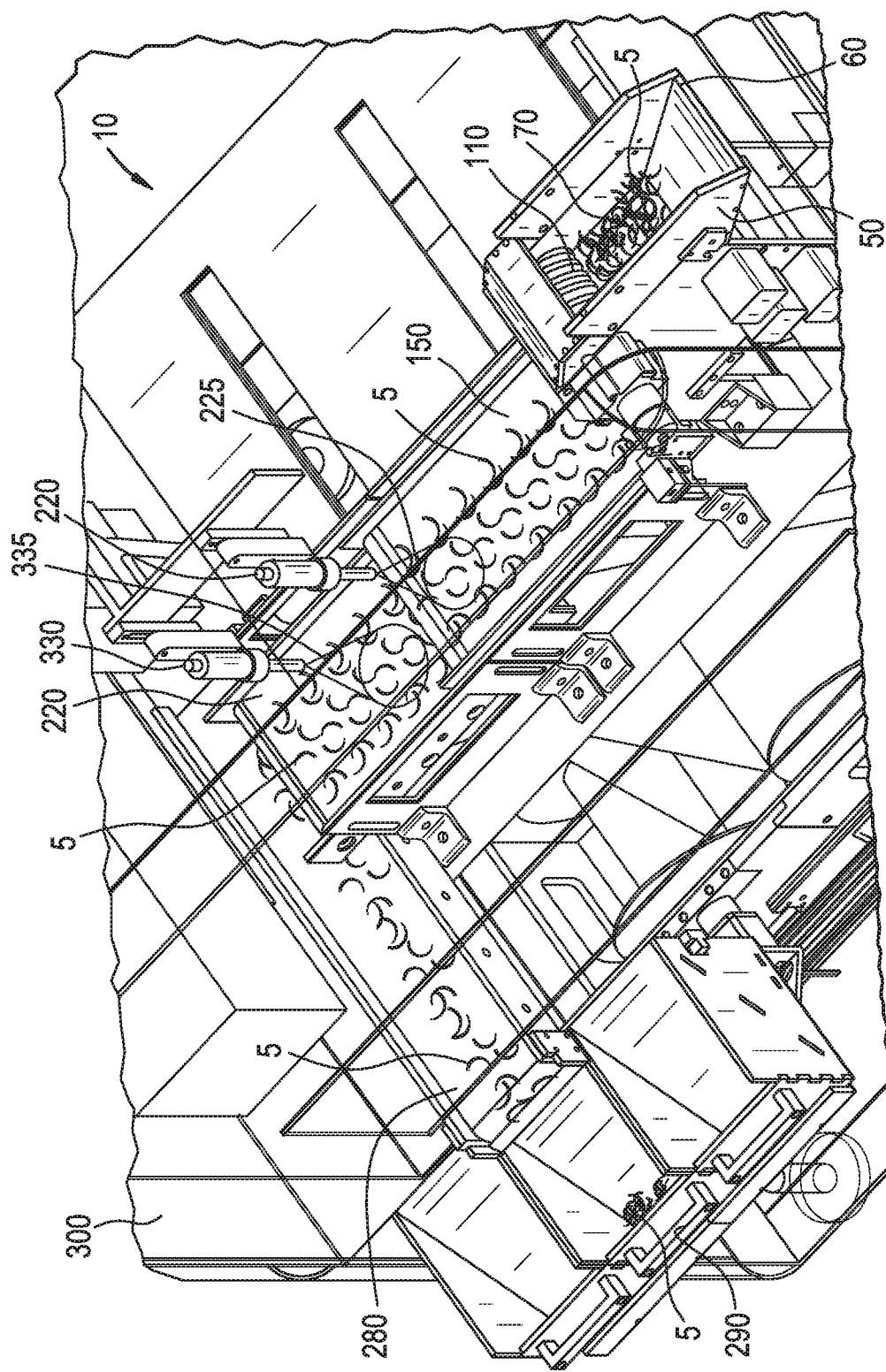
FIG. 14 is a perspective view of the apparatus of FIG. 9 illustrating the needle discharge conveyor and the coated needle collection bins.
Figure 15:
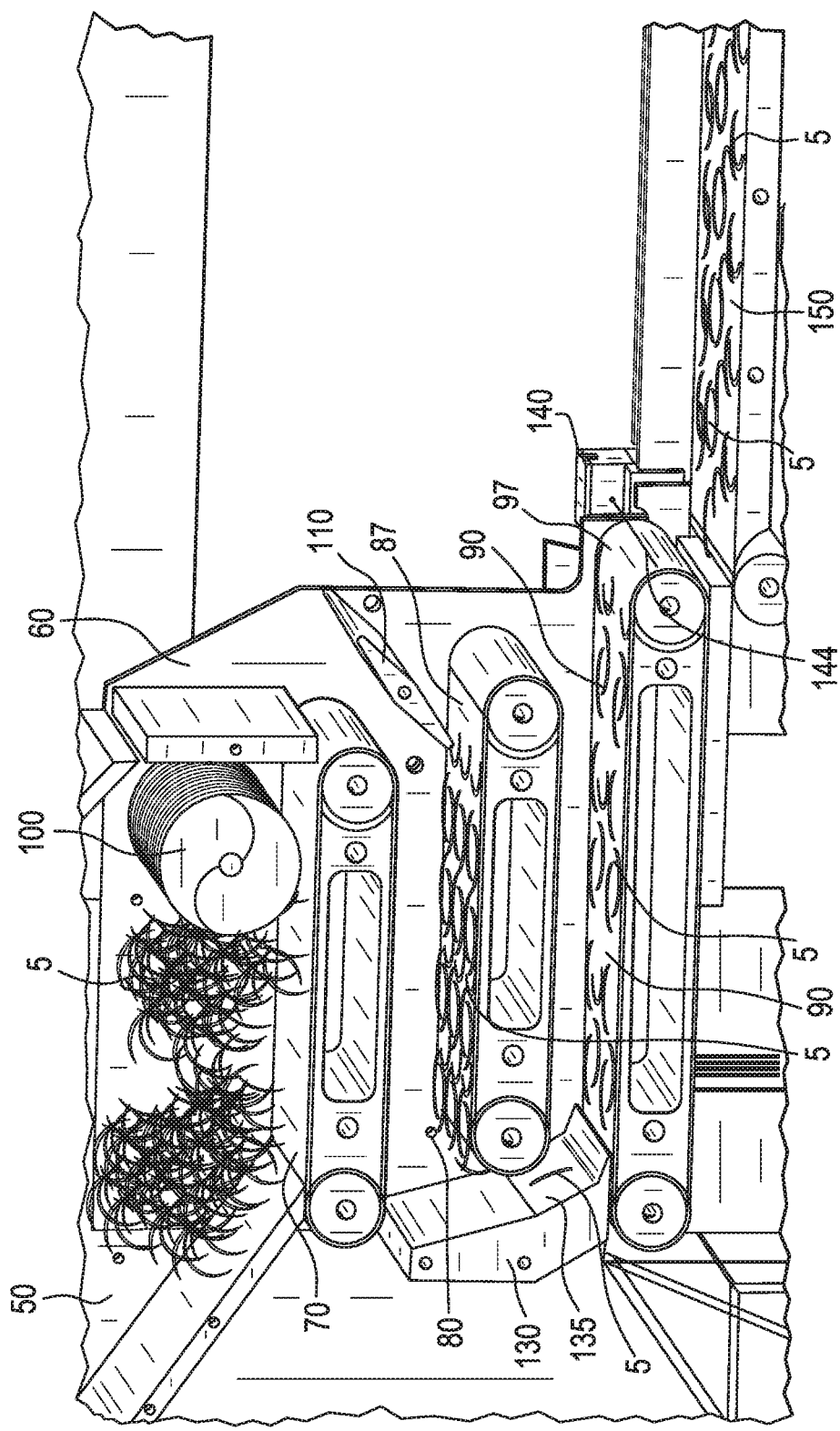
FIG. 15 is a magnified cut-away view of the needle separation tower of FIG. 13.
Figure 16:
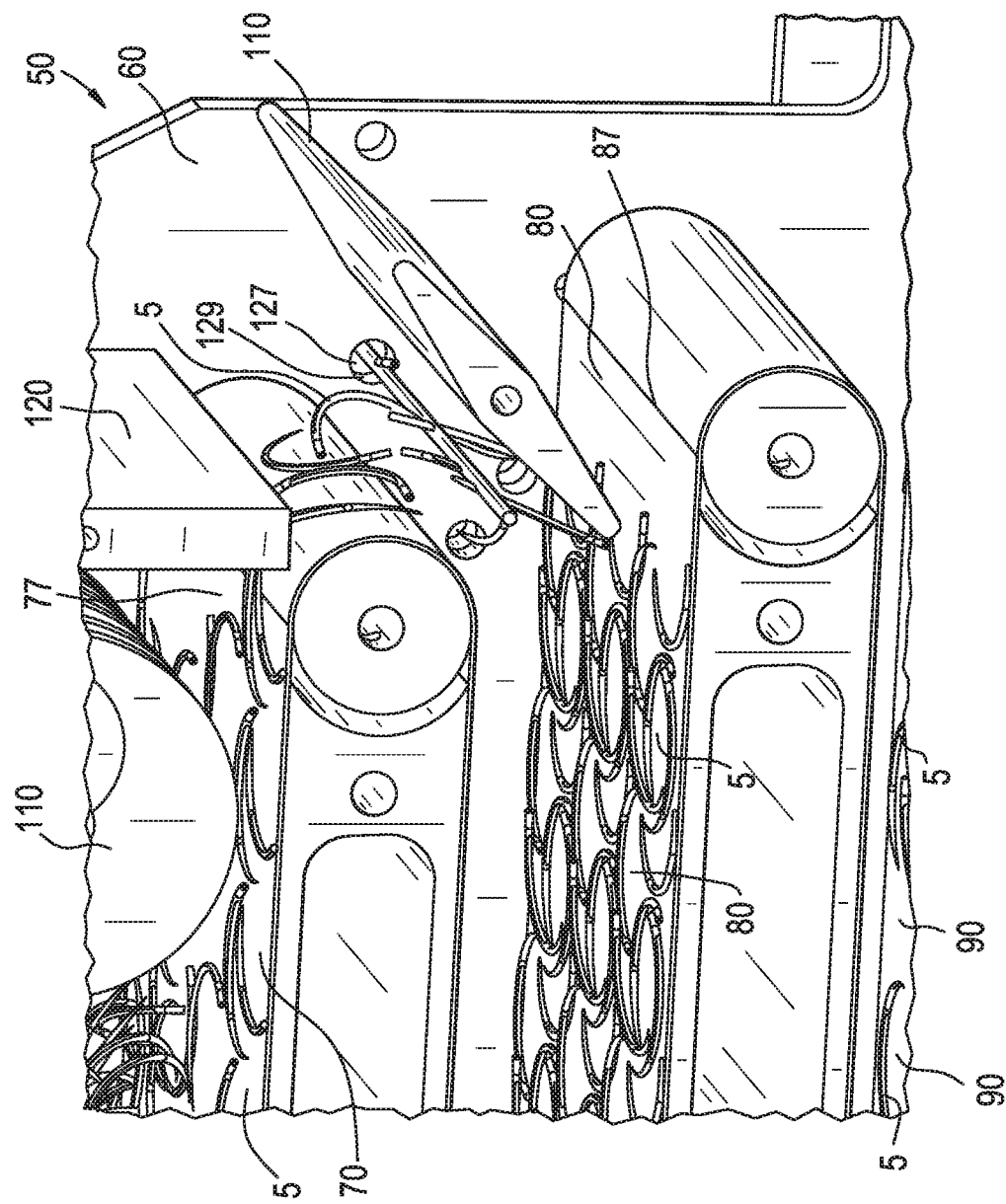
FIG. 16 is a partial magnified view of the needle separation tower of FIG. 15 showing the flow of needles falling from the top tower belt, through the laser beam of the needle flow sensor system, onto the barrier member, and then onto the middle tower belt.
Figure 17:
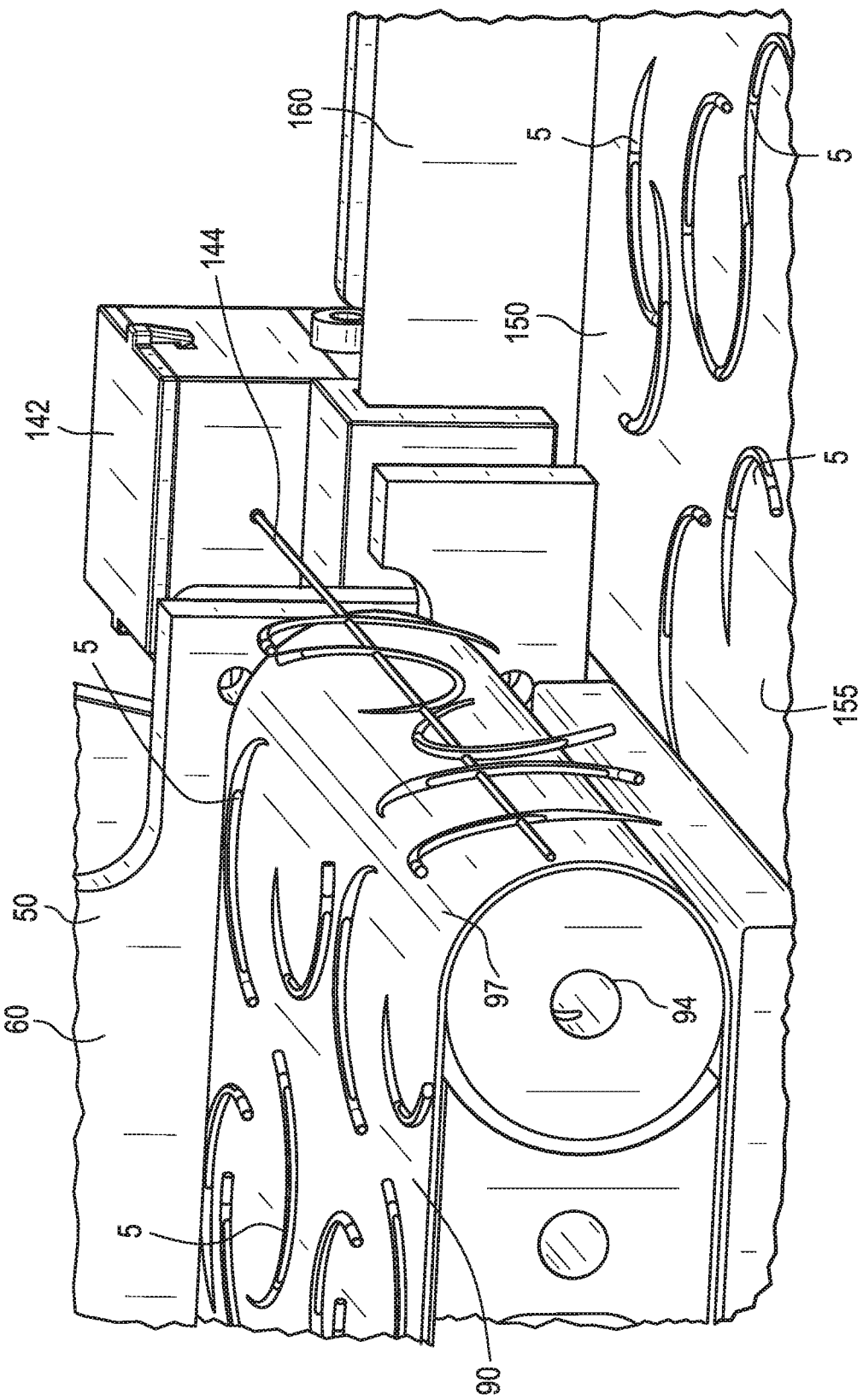
FIG. 17 is a partial magnified view of the needle separation tower of FIG. 15 showing the flow of needles falling from the bottom tower belt, through the laser beam of the laser beam sensor system, onto the upper paper belt of the upper paper conveyor.

The bulk needle spray apparatus of the present invention is illustrated in FIGS. 1-17. Referring to FIGS. 1A-D, the apparatus 10, which utilizes an ASYMTEK SL-940 Conformal Coating system with specific modifications to allow for the present use, is seen to have frame 20 having top surface 22. Mounted to top surface 22 at end 24 is the needle separation tower 50. Also mounted to the top surface 22 of frame 20 are the upper paper conveyor 150 and the lower paper conveyor 220. Adjacent to the end of the lower paper conveyor 220 is the discharge conveyor 280. As also seen in FIGS. 2 and 3, separation tower 50 is seen to have frame 60. Mounted to frame 60 are the top tower belt 70 having first end 76 and second end 77, the intermediate or middle tower belt 80 having first end 86 and second end 87, and the bottom tower belt 90 having first end 96 and second end 97. Top tower belt 70 has top side 71 and bottom side 75; middle tower belt 80 has top side 81 and bottom side 85; and, bottom tower belt 90 has top side 91 and bottom side 95. Mounted to the top of frame 60 is the cylindrical brush member 100. Brush member is driven in a rotating manner by drive motor 108 in the direction of arrow 109. Frame 60 is seen to have a top needle loading ramp 62 extending over first end 76 of top tower belt 70. The ramp 62 is sufficiently angulated to effectively allow bulk needles to slide in a downward manner and fall upon the end 76 of top tower belt 70. Adjacent to the opposite second end 77 of top tower belt 70 and mounted to frame 60 is the angled baffle 110. Situated adjacent to the brush member 100 and mounted to frame 60 over the second end 77 of belt 70 is the adjustable gate member 120. The bottom 122 of gate member 120 can be moved up or down to a fixed position relative the end of top tower belt 70. Gate member 120 is a plate that is moveably mounted to frame 50 by screws which are threaded into both sides of the gate member 120 and which pass through slots in the frame 60 to allow for vertical adjustment. Needles passing through the gap 124 created between the bottom 122 of gate member 120 and the top of top tower belt 70 are directed to angled baffle 110 which is sufficiently angled to effectively change the direction of needles falling from top tower belt 70 and direct the needles to the second end 87 of middle tower belt 80.

Mounted to frame 60, next to second end 77 and adjacent to and below gate member 120 is the needle flow sensor system 125. Needle flow sensor system 125 includes two separate components: flow laser emitter 127 and flow sensor receiver 128. Emitter 127 and sensor 128 are mounted on opposite sides of frame 60. Flow laser emitter emits a laser light beam 129. The needle flow sensor 125 is positioned in such a way that the laser light beam 129 generated by the flow laser emitter 127 is focused onto the flow sensor receiver 128, thereby generating a signal which is read by a microcontroller and represents the amount of light picked up by the flow sensor receiver 128. Because of the proximity of the needle flow sensor 125 to the second end 77 of the top tower belt 70, needles falling from the second end 77 to tower belt 80 will pass, at least in part, through the laser beam 129. As a portion of a needle obscures the laser beam 129, the amount of light which reaches the flow laser receiver 128 is reduced, thereby causing a reading of lower light intensity to be read by the microprocessor. The microprocessor counts the number of needles which pass through the needle flow sensor 125 over a fixed time interval. This needle count (n) per time interval is then used to adjust the speed of the top tower belt 70 by comparing the actual needle count to a pre-programmed set of ranges: e.g., $n \leq 12$, $13 \leq n < 15$, $16 \leq n < 34$, $n \geq 35$. The speed of the top tower belt 70 is constantly monitored and updated after each recurring time interval. This permits real-time adjustments to the overall flow of needles through the needle separation tower 50 and maintains a more consistent throughput. Needle flow sensor 125 can be made from conventional, commercially available laser emitters and sensor receivers such as the OMRON E32-T11N and E3X-HD11 modules available from ALLIED ELECTRONICS.

Adjacent to the first end 86 of the middle tower belt 80 and mounted to frame 50 is the overspill barrier member 130. Barrier member 130 is seen to be a plate-like member having upper vertical section 132 and lower ramp section 135. The ramp section 135 is sufficiently angulated to effectively allow bulk needles to slide in a downward manner and fall upon the first end 96 of bottom tower belt 90.

Top tower belt 70 is seen to be a continuous belt mounted to drive roller 72 and roller 74. Drive motor 73 is seen to be mounted to frame 60 and connected to drive roller 72. Top tower belt 70 is seen to have an overall movement in the direction of arrow 79. Top tower belt 70 is preferably made from silicone rubber, for example part number 86528569 from MSC DIRECT, in order to provide ample traction through the first separation step as the needles encounter the rotating brush member 100, for example part number 7221T28 from MCMASTER-CARR. Other conventional materials that can be used to make the top tower belt 70 include polyurethanes, natural, or synthetic rubber, and the like. Top tower belt 70 will provide a surface that has sufficient friction (i.e., coefficient of friction) to effectively move a pile of needles, but is soft enough to effectively prevent damage to needles. Middle tower belt 80 is seen to be a continuous belt mounted to drive roller 82 and roller 84. Drive motor 83 is seen to be mounted to frame 60 and connected to drive roller 82. Middle tower belt 80 is seen to have an overall movement in the direction of arrow 89. Middle tower belt 80 is preferably a composite belt made with a Teflon outer layer bonded to a silicone layer prepared according the procedure described in U.S. Pat. No. 7,939, 615, e.g., CHEMFAB® Belts available from Saint Gobain Performance Plastics. The middle tower belt 80 will have an ultra-low friction surface (i.e., low coefficient of friction) to allow the needles to spread out, while the inner silicone layer provides enough friction to the driving roller to drive the belt. Other conventional materials that can be used to construct middle tower belt 80 include other composite combinations which provide one low friction surface with a high friction surface and the like. Bottom tower belt 90 is seen to be a continuous belt mounted to drive roller 92 and roller 94. Drive motor 93 is seen to be mounted to frame 60 and connected to drive roller 92. Bottom tower belt 90 is seen to have an overall movement in the direction of arrow 99. Bottom tower belt 90 is preferably made from the same materials as that of middle tower belt 80 in order to have the same or a similar ultra-low friction surface. Other conventional materials that can be used to make the bottom tower belt 90 include composite combinations which provide one low friction surface with a high friction surface and the like. The cylindrical brush member 100 is preferably a soft bristle brush made from bristles 105, and having a variety of conventional brush patterns and bristle stiffnesses. The bristle stiffnesses and brush patterns will be selected to provide sufficiently effective separation of needles of different sizes and shapes. Both helical and spiral patterns may be used for the brush bristle pattern. The gap between each line of bristles is sufficient, e.g., between 2 to 20 mm, to effectively accommodate different sizes and shapes of needles. The length of bristle is in the range, for example, of between 0.5 to 3 inches, to effectively provide for the same purpose. As shown in FIGS. 2 and 3, the brush 100 is seen to have a helical pattern. The bristles of brush member 100 can be made from conventional materials including nylon, polyester, and other polymers and natural fiber and the like. The brush 100 can be adjusted to change the size of the gap 106 between the outer periphery 107 of brush 100 and the outer side 71 of top tower belt 70.

The drive motors 73, 83 and 93 are preferably conventional DC stepper motors. The DC stepper motors are programmed to provide back and forth oscillatory motion while progressively moving the belt in an overall forward manner. Conventional DC stepper motors that can be used in the apparatus 10 of the present invention include the 17HD48002H-22B NEMA 17 stepper motor manufactured and supplied by ZYLtech ENGINEERING, LLC, located in Spring, Tex., and available from Amazon.com. Drive motor 108 is a conventional DC geared motor controlled by a Pulse Width Modulation (PWM) controller in order to increase or decrease the RPM of the brush.

Mounted to frame 60 adjacent to the second end 97 of belt 90 is the laser beam sensor system 140. Laser beam sensor system 140 consists of light emitting diode (LED) laser beam source 142 emitting laser beam 144 and photoelectric cell receiver 146 for receiving the laser beam 144. LED laser beam source 142 is seen to be mounted to one side of frame 60 while the photoelectric cell receiver 146 is mounted on the other side or opposite side of frame 60 in alignment with laser beam 144 such that needles falling off of the end 97 of lower tower belt 90 pass through the laser beam 144. Laser beam sensor 140 is connected to a conventional microprocessor to read electrical signals generated by photoelectric cell receiver 146. Laser beam sensor 140 can be made from conventional, commercially available LED lasers and photoelectric receivers such as, for example, a 650 nm Laser Sensor Module 6 mm 5V 5 mW Red Laser Dot Diode and a Phantom YoYo Arduino compatible Light Sensor available from Amazon.com.

Referring to FIGS. 1-8, adjacent to the needle separation tower 50 are the upper paper conveyor 150 and the lower paper conveyor 220. Upper paper conveyor 150 is seen to have upper paper belt 155 made from an absorbent material, preferably Kraft Paper. Other conventional materials that can be used in addition to Kraft paper include absorbent materials such as cloth or other non-woven natural or synthetic material that provides ample absorption of overspray and the like, however it is preferred that the upper paper belt 155 be a single use, disposable belt. Upper paper conveyor 150 is seen to have first end 152 and second end 154. Upper paper conveyor 150 is seen to have upper frame 160 and lower frame 210. Drive roll 200 and driven roll 190 are mounted to lower frame 210. Mounted to the upper frame 160 are the idle rollers 172 and 174, end rollers 182 and 184, and tension roller 188. End roller 184 is constructed to have magnetic properties. This may be done in a variety of conventional manners including, for example, by mounting a magnetic polymeric composite material about the outer periphery of roller 184. Other conventional manners for making roller 184 magnetic include the use of a solid metal roller which has been magnetized to an adequate pull strength. Preferably, the magnetic field of roller 184 is strong enough to effectively attract and hold a needle but sufficiently weak to be exceeded by the weight of a needle, such that gravity will cause the needle to separate from the paper belt 155 thereby flipping the needle onto its coated side as the paper moves about and away from the roller on the underside of the conveyor. The magnetic material used possesses a relatively low magnetic pull strength between 0.90-1.36 lb/in$^2$. This will typically be a flexible magnetic tape, although other conventional magnetic materials may be used. The pull strength of the magnetic material will sufficiently effective to provide the desired properties and will typically range, for example, from about 0.3 to about 4 lb/in$^2$, more typically about 0.6 to about 2 lb/in$^2$, and preferably about 0.8 to about 1.4 lb/in$^2$.

Upper paper belt 155 is seen to come off of driven roll 190, move over idle roller 172, pass between first end roller 182 and tension roller 188, move along the top of frame 160 to second end roller 184, then move down about second idle roller 174, and finally is taken up by drive roll 200. Drive roll 200 is driven by a conventional geared stepper motor 205, for example such as 17HD48002H-05.18 NEMA 17 stepper motor manufactured and supplied by ZYLtech ENGINEERING, LLC, located in Spring, Tex., and available from Amazon.com.

The lower paper conveyor 220 is seen to be adjacent to and at a lower height than the upper paper conveyor 150. Lower paper conveyor 220 is seen to have lower paper belt 225 made from an absorbent material, preferably Kraft Paper similar or identical to belt 155. Other conventional materials that can be used in addition to Kraft paper include absorbent materials such as cloth or other non-woven natural or synthetic material that provides ample absorption of overspray and the like, however it is preferred that the lower paper belt 225 be a single use, disposable belt. Lower paper conveyor 220 is seen to have first end 222 and second end 224. Lower paper conveyor 220 is seen to have upper frame 230 and lower frame 270. Drive roll 250 and driven roll 240 are mounted to lower frame 270. Mounted to the upper frame 230 are the idle rollers 242 and 244, end rollers 262 and 264, and tension roller 268. Lower paper belt 225 is seen to come off of driven roll 240, move over idle roller 242, pass between first end roller 262 and tension roller 268, move along the top of frame 230 to second end roller 264, then move down about second idle roller 244, and finally is taken up by drive roll 250. Drive roll 250 is driven by a conventional geared stepper motor 255, for example such as 17HD48002H-05.18 NEMA 17 stepper motor manufactured and supplied by ZYLtech ENGINEERING, LLC, located in Spring, Tex., and available from amazon.com.

The upper and lower paper belts 155 and 255 will move at a speed sufficiently effective to allow for a sufficiently effective coating to be applied as well as allow a sufficient amount of time for excess silicone coating to be absorbed by the absorptive belts 155 and 255.

Seen beneath the end of lower paper belt 225 adjacent to second end roller 264 is the discharge conveyor 280 having end 284 situated over needle catch bins 290.

Kraft paper is preferably used as a conveying material for upper and lower absorbent paper belts 155 and 225 because it effectively absorbs overspray from the coating application process. This prevents the formation of high concentrations of silicone from accumulating which may stick or adhere the needles to the surfaces of the upper and lower paper belts and prevent them from easily releasing from the surfaces. Also, since the paper is preferably used only once and discarded when the driven spools or rolls 190 and 240 are empty, there is no need to have to clean off the surface as would be necessary with a continuous belt. Alternative absorbent materials may also be used for belts 155 and 225 as previously mentioned above. Preferably, the driven spools consist of a roll of Kraft paper having a central cardboard tube, while the drive spools consist of empty cardboard tubes.

The coating apparatus 10 of the present invention is seen to be enclosed in an outer cell housing 300. Mounted to top interior surface 305 of outer housing 300 is the coating system 310 having spray heads 320 and 330. The spray heads 320 and 330 are connected to a conventional automatic coating system (not shown) such as a NORDSON ASYMTEK Conformal Coating System with dual overhead spray applicators, Model SL-941 available from nordson.com. This system provides a self-contained cell or outer housing 300 which houses the equipment for coating the needles, including spray heads 320 and 330 and apparatus 10. It will be appreciated by those skilled in the art that although two spray heads are preferred in the practice of the present invention, a single spray head or more than two spray heads may be used.

The apparatus 10 of the present invention is prepared for coating needles in the following manner. Driven paper roll 190 containing upper paper belt 155 is loaded into lower frame 210. The upper paper belt 155 is then threaded up and about idle roller 172, then over tension roller 188 and around first end roller 182, moved along the top of frame 160 to and about second end roller 184, then down about second idle roller 174, and finally down to drive roll 200 where it is engaged or connected. Driven paper roll 240 containing lower paper belt 225 is loaded into lower frame 270. The lower paper belt 225 is then threaded from driven roll 240 over idle roller 242, then over tension roller 268 and around first end roller 262, moved along the top of frame 230 to second end roller 264, then moved down and about second idle roller 244, and finally down to drive roll 250 where it is engaged or connected. The conventional silicone coating solution tank that is part of the spray system (not shown) is filled with a sufficiently effective quantity of silicone spray solution. Next, the outer cell housing 300 is closed to encapsulate the apparatus 10.

The bulk needle spray coating apparatus 10 of the present invention operates in the following manner as illustrated in FIGS. 9-16. Surgical needles 5 are supplied to the apparatus 10 in boxes of varying quantities depending on the sizes and shapes of the needles. To begin the process of coating a batch of needles 5, the appropriate quantity of a specific needle type is selected and loaded in a bulk manner into the top level of the needle separation tower 50 by dumping the needles 5 onto needle ramp 62. The needles 5 are guided down needle ramp 62 which is set at an angle such that the needles will be allowed to freely proceed down the needle ramp 62, as well as provide a surface for needles to be piled onto, thereby increasing the overall capacity of the needle separation tower 50. The needles 5 are then deposited by gravity from needle ramp 62 onto the first end 76 of top tower belt 70. The top tower belt 70 is driven by drive motor 73, a DC stepper motor which is programmed to oscillate back and forth while still progressing in a forward manner overall in the direction of arrow 79. This is accomplished by driving the drive motor 73 forward for a given amount of time, and then driving rearward for an amount of time which is less than that of the forward drive time. This motion is repeated at a rate sufficient to cause a vibration within the pile of the needles 5, allowing them to begin to move apart and separate from each other in the pile. As the needles 5 are carried forward in the direction of arrow 79, they encounter a rotating soft cylindrical brush 100 at the second end 77 of top tower belt 70, which is set to rotate in a direction 109 counter to the mean overall progression (arrow 79) of the top tower belt 70. The soft cylindrical brush member 100 is used to regulate the quantity of needles 5 which exit off of the second end 77 of top tower belt 70 at any given time by adjusting the rotational speed at which brush member 100 rotates as well as adjusting the clearance gap 106 between the outer periphery 107 of cylindrical brush member 100 and the outer surface 71 of top tower belt 70. Different patterns and bristle stiffnesses are available for the soft cylindrical brush 150 to separate needles 5 with different sizes and shapes. After moving past cylindrical brush member 100, the needles 5 must pass through the gap 124 under the bottom 122 of adjustable gate member 120 before dropping off of the second end 77 of the top tower belt 70. The adjustable gate member 120 is another method for controlling the quantities of needles 5 that are allowed to proceed to the next lower level of the needle tower 50, which is the intermediate tower belt 80. The adjustable gate member 120 can be raised or lowered vertically in order to provide a larger or smaller gap 124 for the needles 5 to pass through. After passing through gap 124, the needles 5 pass through laser light beam 129 of needle flow sensor 125. The needles 5 are counted by the needle flow sensor 125 and a connected microprocessor; the number of counted needles 5 is used to control the speed of top tower belt 70.

After passing through the gap 124 below adjustable gate member 120 and passing through needle flow sensor 125, the needles 5 are directed onto the second end 87 of middle tower belt 80 by the angled baffle member 110. The angled baffle member 110 is used to prevent the needles 5 from exiting the needle tower 50 at the wrong time, and also functions to change the direction of travel of the needles 5 as they land on the second end 87 of middle tower belt 80. The middle tower belt 80 travels in a direction indicated by arrow 89 opposite that of the top tower belt 70. The ultra-low friction surface of outer side 81 of middle tower belt 80 allows the needles 5 to spread out as they land on the outer surface 81 of the middle tower belt 80, yet effectively engages the needles 5 on belt 80 to move them in the intended direction 89 of travel. The middle tower belt 80 is driven by drive motor 83 which provides the ability to drive the belt at a constant speed or with an oscillation type drive as utilized with the top tower belt 70 with a mean progression in direction 89.

As the needles 5, which are now more singulated and spaced apart from each other on surface 81, drop off the first end 86 of the middle tower belt 80, they encounter the overspill barrier member 130 which prevents the needles 5 from falling out of the end of the needle separation tower 50 and also functions to change the direction of travel of the needles 5 as they slide down ramp section 135 and are directed to land on the first end 96 of the bottom tower belt 90. Lower tower belt 90 is made from the same material as that of middle tower belt 80 having an ultra-low friction surface 91. The overall speed of travel of each of the successively lower belts in the needle separation tower 50 is maintained at a rate which exceeds that of the belt above it in order to further spread out the needles 5 as they pass from one level to the next. The bottom tower belt 90 works to change the direction of travel of the needles 5 once again in the direction indicated by arrow 99, as well as to further separate the needles 5 from each other (i.e., space apart and/or singulate), and is driven by drive motor 93 which provides the ability to drive the lower tower belt 90 at a constant speed or with an oscillation type drive as utilized with the top tower belt 70. After traversing the length of the bottom tower belt 90, the needles 5 drop from the second end section 97 onto the upper paper belt 155 of the upper paper conveyor 150.

When the needles 5 drop from the second end 97 of the bottom tower belt 90 onto the paper belt 155 of upper paper conveyor 150, they pass through the laser beam 144 of laser beam sensor 140. The laser beam sensor 140 is positioned on frame 60 in such that the laser beam 144 generated by the LED laser beam source 142 is focused onto the photo electric cell receiver 146, thereby generating an electrical pulse which produces a signal that is read by a microcontroller and represents the amount of light picked up by the photoelectric cell receiver 146. Furthermore, because of the proximity of the laser beam sensor 140 to the second end 97 of the bottom tower belt 90, as needles 5 fall off from the second end 97 of bottom tower belt 90 onto the upper paper belt 155 of the upper paper conveyor 150, at least some part of the needle will pass through the laser beam 144. As a portion of a needle obscures the laser beam, the amount of light which reaches the Photoelectric cell receiver 146 is reduced or diminished, thereby causing a reading of lower light intensity to be read by the microprocessor which is in turn used to signal the upper paper conveyor 150 and the lower paper conveyor 220 to begin moving. Once the paper conveyors have been triggered to begin running, they will run for a predetermined period of time which will effectively allow the needles 5 to pass fully the lengths of the upper and lower paper conveyors 150 and 220, but not so long as to cause an excess waste of paper travelling without the presence of needles 5. After the predetermined time period has expired, the microprocessor orders the conveyors 150 and 220 to turn off and stop.

As the needles 5 land on the top of paper belt 155 of upper paper conveyor 150 at first end 152, they have been predispersed and regulated by the multiple tiers of the needle separation tower 50 to substantially ensure that there is space between the needles 5 and there are substantially and effectively few if any opportunities for the needles 5 to be situated in a manner where they cross or lay across one another. As the needles 5 travel across the belt 155 of upper paper conveyor 150, the spray nozzles 320 and 330 begin to move and spray a fine atomized mist of silicone in substantially cone-shaped configurations 325 and 335 over the area that comprises the second end 154 of the upper paper conveyor 150 and the beginning or first end 222 of the lower paper conveyor 220. The spray nozzles 320 and 330 may optionally spray silicone coatings along the entire lengths of the upper and lower paper conveyors 150 and 220. The spray system which consists in part of the nozzles 320 and 330 as well as adjunct pumping equipment and controls may be manually actuated or may be automatically actuated by a conventional controller receiving a signal from a detection instrument, for example, the laser beam sensor 140. The nozzles may operate in a predetermined pattern or a pattern generated by an algorithm depending upon the quantities and types and distributions of needles on the paper belts. The upper and lower paper conveyors 150 and 220 are driven at a constant rate which is effectively optimized to ensure complete and even coverage of the needles 5 with the lubricious silicone coating. At the second end 154 of the upper paper conveyor 150, the needles 5 on paper belt 155 are engaged by the magnetic field of end roller 184. The magnetic material of the end roller 184 provides a relatively low holding force that is sufficiently effective and is merely used to hold the needles 5 (which are composed of a magnetic form of stainless steel) in contact with the surface of the paper belt until the belt and needles 5 move around roller 184 to the vertical position and then horizontal position, thereby flipping the needles 5 over as they wrap 180° around the roller 184. The relatively low holding force (e.g., between 0.90-1.36 lb/in$^2$) of the magnetic roller 184 is overcome by the weight of the needles 5, allowing the needles 5 to drop off onto the paper belt 225 of the lower paper conveyor 220 at first end 222 as the needles 5 travel beyond the reach of the magnetic adhesion of the roller. The needles 5 are now positioned onto the lower paper conveyor 220 on top of paper belt 225 with their uncoated surfaces facing up, ready to be coated on the remaining uncoated side. As the needles 5 travel across the paper belt 225 of lower paper conveyor 220, the spray nozzles 320 and 330 begin to move and spray a fine atomized mist of silicone coating composition over that area of paper belt 225 that results in an applied uniform silicone coating.

After receiving the final coating, the needles 5 are dropped off the second end 224 of the lower paper conveyor 220 onto the discharge conveyor 280. This discharge conveyor 280 runs at a constant speed and carries the needles 5 outside of the outer cell housing 300, where they drop into the needle catch bins 290. From here the needles 5 will be moved and additionally processed to receive their final curing to set the lubricious coating on the surface of the needles 5, and then sent for final processing.

The needles coated by the process of the present invention using the apparatus of the present invention have uniform coatings on all exterior surfaces. This can be attributed in part to the combination of the sorting process, the spray coating process, the absorbent paper belts that carry the needles during the coating process, and the flipping action of the magnetic roller that places the uncoated sides of the needles in a position to be spray coated. The needles coated by the novel bulk needle coating process of the present invention have many advantages including uniform coatings, superior needle tip coatings, fewer defects, and shorter processing times. In addition, the novel process provides for production and manufacturing efficiencies by reducing silicone coating composition waste, eliminating or substantially reducing defective coatings requiring finished needles to be discarded, improving the penetration performance of the needles, and providing a better more consistent product to the customer.

The droplet sizes of the silicon coating composition solution sprayed from the spray nozzles 320 and 330 will be sufficient to provide for effective coating coverage of the needle tip and body. The viscosities of the silicone coating solutions useful in the practice of the present invention will typically range, for example, from about 40 cPs to about 250 cPs, more typically about 60 cPs to about 300 cPs, and preferably about 80 cPs to about 160 cPs. The solids content of the coating solutions useful in the practice of the present invention will be sufficient to provide for effective covering of the needle tip and body. Typically, the solids content will range, for example, from about 4% to about 15%, more typically about 6% to about 12%, and preferably about 8% to about 10%.

The coating thicknesses of silicone coatings on coated needles using the apparatus and processes of the present invention will be sufficient to provide effective needle penetration performance. Typically, the coating thicknesses will range from about 0.1 micron to about 4 micron, more typically about 0.3 micron to about 3 micron, and preferably about 0.5 micron to about 2 micron. The surgical needles that can be coated by the novel apparatus and method of the present invention will be conventional surgical stainless steel surgical needles made from alloys such as ETHAL- LOY®, 420, 4310, 420 and/or 455, as well as needles made from tungsten-rhenium alloys or Nitinol. The sizes of the needles that can be coated will vary and will include conventional needle sizes that, for example, may range from approximately 0.014 inches to about 0.070 inches in wire diameter.

The following examples are illustrative of the principles and practice of the present invention, although not limited thereto.

Example 1 (Coating Formulations)

Example 1a

Two types of surgical needles were coated using the bulk spray coating apparatus of the present invention with a silicone coating composition consisting of a mixture of the silicone components summarized in Table 1a.

TABLE 1a

Coating Formulation of Example 1a.

| Component | Trade Name | Weight (g) |
| --- | --- | --- |
| Trimethylsilyl-terminated polydimethylsiloxane | Gelest DMS T72 | 96 |
| dimethylvinyl silyl-terminated polydimethylsiloxane | Gelest DMS V52 | 96 |
| Platinum catalyst 0.02% solution | Gelest SIP in 1% xylene | 38.4 |
| Trimethylsilyl-terminated polymethylhydrosiloxane | Gelest DMS HMS 991 | 1.92 |
| Solvent 1 | Xylene | 407.7 |
| Solvent 2 | Heptane | 1760 |

The coating composition was mixed in a conventional mixing vessel using a conventional mixing agitator.

Example 1b

Two types of surgical needles were coated using the bulk spray coating apparatus of the present invention with a silicone coating composition consisting of a mixture of the silicone components summarized in Table 1b.

TABLE 1b

Coating Formulation of Example 1b.

| Component | Trade Name | Weight (g) |
| --- | --- | --- |
| Silicone raw material | Nusil MED 4162 | 534 |
| Solvent | Heptane | 1466 |

The coating composition was mixed in a conventional mixing vessel using a conventional mixing agitator.

Example 2

Coating of ETHICON 40 mil CT-1 Surgical Needles, Needle Code: 4840155

Example 2a

CT-1 Surgical Needles Coated with the Coating Solution of Example 1a 3,000 uncoated ETHICON 40 mil CT-1 surgical needles available from ETHICON, Inc., Somerville, N.J. 08876 were fed in a bulk manner into the needle separation tower of the bulk spray coating apparatus of the present invention described above. The needles were separated by the separation tower and entered into the spray zone and were coated with the silicone coating composition of Example 1a. The coated needles were cured in an oven at 195° C. for 2 hrs.

A control sample was also prepared for the purpose of comparison. A batch of surgical needles from the same lot of CT-1 surgical needles was dipped into a 10% Nusil MED4162 heptane solution, drained, dried, and cured at 190° C. for 2 hours.

Conventional surgical needle penetration testing was performed on these two sets of needles as described in the testing section. The results are from penetration testing done using 30 individual needles. The coated needles were penetrated 20 times each. The average penetration force for each pass is summarized in Table 2a.

TABLE 2a

Needle Penetration Test
Coated Needles of Example 2a

| Penetration # | Avg. Force (g) Example 2a | Avg. Force (g) Control Sample |
| --- | --- | --- |
| 1 | 120 | 119 |
| 10 | 133 | 177 |
| 20 | 135 | 210 |

Example 2b

CT-1 Surgical Needles Coated with the Coating Solution of Example 1b 3,000 uncoated ETHICON 40 mil CT-1 needles were fed in a bulk manner into the needle separation tower of the bulk spray apparatus of the present invention described above. The needles were initially separated by the needle separation tower and then entered into the spray zone and were coated with the silicone coating composition of Example 1b. The coated needles were cured in an oven at 195° C. for 2 hrs.

A control sample was also prepared for the purpose of comparison. A batch of uncoated needles from the same lot CT-1 needles was dipped into a 10% Nusil MED4162 heptane solution, drained, dried, and cured at 190° C. for 2 hours.

Conventional surgical needle penetration testing was performed on these two sets of needles as described in the testing section. The results are from penetration testing done using 30 individual needles. The coated needles were penetrated 20 times each. The average penetration force for each pass is summarized in Table 2b.

TABLE 2a

Needle Penetration Test
Coated Needles of Example 2b

| Penetration # | Avg. Force (g) Example 2b | Avg. Force (g) Control Sample |
| --- | --- | --- |
| 1 | 125 | 119 |
| 10 | 133 | 177 |
| 20 | 148 | 210 |

Example 3a

24 mil MH Needles Coated with the Coating of Example 1a 3,000 uncoated ETHICON 24 mil MH needles (available from ETHICON, Inc.) were fed in a bulk manner into the needle separation tower described above. The needles were separated by the tower and entered into the spray zone and were coated with the coating composition of Example 1a. The coated needles were cured in an oven and cured 195° C. for 2 hrs.

A control sample was also prepared for the purpose of comparison. Needles from the same lot of MH needles were dipped into a 10% Nusil MED4162 heptane solution, drain, dried, and cured at 190° C. for 2 hour.

Conventional surgical needle penetration testing was performed on these two sets of needles as described in the testing section. The results are from penetration testing done using 30 individual needles. The coated needles were penetrated 20 times each. The average penetration force for each pass is summarized in Table 3a.

TABLE 3a

Needle Penetration Test: Example 3a

| Penetration # | Avg. Force (g) Example 2 | Avg. Force (g) Control Sample |
|---|---|---|
| 1 | 69 | 121 |
| 10 | 94 | 180 |
| 20 | 106 | 231 |

All of the examples above indicated that needles coated using the apparatus and processes of the present invention, as described herein, provided superior penetration performance compared to those needles coated with a conventional batch dipping process.

Although this invention has been shown and described with respect to detailed embodiments thereof, it will be understood by those skilled in the art that various changes in form and detail thereof may be made without departing from the spirit and scope of the claimed invention.

We claim:

1. An apparatus for spray coating bulk surgical needles, comprising:
    a needle separation tower for receiving bulk surgical needles and separating the needles, the needle tower comprising:
        a tower frame having a top, a bottom, a first end and a second end;
        a top tower belt, an intermediate tower belt, and a bottom tower belt mounted to the tower frame, each belt having a first end and a second end, and a top and a bottom;
        a bulk needle receiving structure associated with the top, first end of the tower frame for receiving a plurality of bulk surgical needles and directing the needles to the top tower belt;
        an angled baffle member for directing needles from the top tower belt to the intermediate tower belt;
        an overspill barrier member for directing needles from the intermediate tower belt to the bottom tower belt;
        a first belt stepper motor engaging the top tower belt;
        a second belt stepper motor engaging the intermediate tower belt;
        a third belt stepper motor engaging the bottom tower belt; and,
        a rotating member mounted to the top of the tower frame at the second end and situated over the top belt for engaging needles on the top belt;
    an upper paper conveyor for receiving needles from the bottom tower belt of the needle separation tower, the upper paper conveyor having a first end and a second end, an upper frame, an upper absorbent belt, an upper drive roll, an upper take-up roll, an upper first end roll and an upper second end roll for engaging needles, and a stepper motor engaging the upper drive roll, the upper second end roll being magnetic;
    a lower paper conveyor for receiving needles from the upper paper conveyor, the lower paper conveyor having a first end and second end, a lower frame, a lower absorbent belt, a lower drive roll, a lower take-up roll, a lower first end roll and a lower second end roll, and a stepper motor engaging the lower drive roll;
    at least one spray nozzle moveably mounted over the upper and lower paper conveyors for spraying a silicone lubricious coating onto surgical needles on the upper and lower absorbent belts.

2. The apparatus of claim 1, additionally comprising a gate member mounted to the needle tower frame adjacent to the second end of the top tower belt.

3. The apparatus of claim 1 wherein the bottom tower belt has a low coefficient of friction surface.

4. The apparatus of claim 1, wherein the top tower belt has a surface having a higher coefficient of friction than the bottom tower belt.

5. The apparatus of claim 1, wherein the intermediate tower belt has a coefficient of friction substantially equal to the coefficient of friction of the bottom tower belt.

6. The apparatus of claim 1 having a laser needle flow counting system for counting needles moving off of the top tower belt and adjusting the speed of the top tower belt.

7. The apparatus of claim 1 having a laser needle flow sensor system for counting needles moving off of the bottom tower belt onto the upper paper conveyor to signal the belts of the upper and lower paper conveyors to start moving.

8. The apparatus of claim 1, wherein the upper second end roll has a length of polymeric magnetic material affixed about at least part of the periphery of the roll.

9. The apparatus of claim 1, additionally comprising an outer shell frame for containing the apparatus.

10. The apparatus of claim 1, wherein the rotating member is a brush.

11. The apparatus of claim 1, wherein the absorbent belts for the upper and lower paper conveyors comprise Kraft paper.

12. The apparatus of claim 1, wherein the movement of the at least one spray head is controlled by a controller to provide a repeatable pattern.

13. The apparatus of claim 1 wherein each belt stepper motor is programmed to provide back and forth oscillatory motion to the respective belt that it engages while progressively moving the belt in an overall net direction.

14. The apparatus of claim 1, additionally comprising a laser sensor system for counting needles exiting the bottom tower belt and controlling the speed of the bottom tower belt.

15. The apparatus of claim 1, wherein the upper and lower paper conveyors additionally comprise a tension roller.

16. The apparatus of claim 1, wherein the intermediate tower belt and the bottom tower belt comprise Teflon bonded to a layer of silicone rubber.

17. The apparatus of claim 1, additionally comprising a discharge conveyor adjacent to the second end of the lower paper conveyor.

18. The apparatus of claim 1, wherein the bulk receiving structure is a ramp member.

19. The apparatus of claim 1, wherein the upper second end roll has a magnetic field strength sufficiently strong to engage and hold a needle on top of the bottom tower belt but sufficiently weak to release a needle on the bottom of the bottom tower belt.

20. The apparatus of claim 8, wherein the polymeric magnetic material has a pull force in the range of about 0.8 to about 1.4 lb/in$^2$.

21. The apparatus of claim 1, wherein the upper second end roll has a pull force strength in the range of about 0.8 lb/in$^2$ to about 1.4 lb/in$^2$.

22. The apparatus of claim 1, wherein the upper and lower absorbent paper belts are single use and disposable.

\* \* \* \* \*